United States Patent
Lorenz et al.

(10) Patent No.: US 9,737,595 B2
(45) Date of Patent: Aug. 22, 2017

(54) COMBINATION OF VACCINATION AND INHIBITION OF MHC CLASS I RESTRICTED ANTIGEN PRESENTATION

(75) Inventors: Christina Lorenz, Basel (CH); Mariola Fotin-Mleczek, Sindelfingen (DE); Karl-Josef Kallen, Tuebingen (DE)

(73) Assignee: CureVac AG, Tübingen (DE)

( * ) Notice: Subject to any disclaimer, the term of this patent is extended or adjusted under 35 U.S.C. 154(b) by 845 days.

(21) Appl. No.: 13/824,502

(22) PCT Filed: Dec. 27, 2011

(86) PCT No.: PCT/EP2011/006585
§ 371 (c)(1),
(2), (4) Date: Jun. 3, 2013

(87) PCT Pub. No.: WO2012/089338
PCT Pub. Date: Jul. 5, 2012

(65) Prior Publication Data
US 2013/0280283 A1    Oct. 24, 2013

(30) Foreign Application Priority Data
Dec. 29, 2010   (WO) ............... PCT/EP2010/007969

(51) Int. Cl.
*A61K 39/00* (2006.01)
*C07K 14/74* (2006.01)

(52) U.S. Cl.
CPC ...... *A61K 39/0011* (2013.01); *A61K 2039/53* (2013.01); *A61K 2039/545* (2013.01); *A61K 2039/55516* (2013.01)

(58) Field of Classification Search
None
See application file for complete search history.

(56) References Cited

U.S. PATENT DOCUMENTS

| | | |
|---|---|---|
| 2005/0032730 A1 | 2/2005 | Von Der Mulbe et al. |
| 2005/0059624 A1 | 3/2005 | Hoerr et al. |
| 2005/0250723 A1 | 11/2005 | Hoerr et al. |
| 2006/0188490 A1 | 8/2006 | Hoerr et al. |
| 2008/0025944 A1 | 1/2008 | Hoerr |
| 2008/0267873 A1 | 10/2008 | Hoerr |
| 2009/0324584 A1 | 12/2009 | Hoerr et al. |
| 2010/0048883 A1 | 2/2010 | Ketterer et al. |
| 2010/0189729 A1 | 7/2010 | Hoerr et al. |
| 2010/0291156 A1 | 11/2010 | Barner et al. |
| 2010/0305196 A1 | 12/2010 | Probst et al. |
| 2011/0053829 A1 | 3/2011 | Baumhof |
| 2011/0250225 A1 | 10/2011 | Fotin-Mleczek |
| 2012/0258046 A1 | 10/2012 | Mutzke |

FOREIGN PATENT DOCUMENTS

| | | |
|---|---|---|
| EP | 1559780 A1 | 3/2005 |
| WO | WO98/25645 A1 | 6/1998 |
| WO | WO2007/105954 A1 | 9/2007 |
| WO | WO2008/069663 A1 | 6/2008 |
| WO | WO2009/008713 A1 | 1/2009 |
| WO | WO 2009/030481 | 3/2009 |
| WO | WO 2009/095226 | 8/2009 |
| WO | WO 2012/013326 | 2/2012 |
| WO | WO 2012/019780 | 2/2012 |
| WO | WO 2012/116714 | 9/2012 |

OTHER PUBLICATIONS

Standley et al (Bioconj. Chem., 2004, 15: 1281-1288).*
Fournier and Schirrmacher (Expert. Rev. Vaccines 8(1); 51-66, 2009).*
Schrieber et al (Seminar. Immunol. 22: 105-112, 2010).*
Klebanoff et al (Immunol. Rev. 2011, 239: 27-44).*
Bringmann et al (J. Biomed. Biotechn. Mar. 2010, ID 623687, pp. 1-12).*
Oosten et al (Intern. Immunol., 2007, 19(9): 1115-1122).*
Chambers B. et al. "Induction of Protective CTL Immunity against Peptide Transporter TAP-Deficient Tumors through Dendritic Cell Vaccination", Cancer Research, vol. 67, No. 18, Sep. 15, 2007, pp. 8450-8455.
Lampen M. H. et al. "CD8+ T Cell Responses against TAP-Inhibited Cells Are Readily Detected in the Human Population", The Journal of Immunology, vol. 185, No. 11, Oct. 27, 2010, pp. 6508-6517.
Van Hall T. et al "Selective cytotoxic T-lymphocyte targeting of tumor immune escape variants", Nature Medicine, vol. 12, No. 4, Apr. 2006, pp. 417-424.
Zwaveling S. et al "Established Human Papillomavirus Type 16-Expressing Tumors Are Effectively Eradicated Following Vaccination with Long Peptides", Journal of Immunology, vol. 169, No. 1, Jul. 1, 2002, pp. 350-358.

* cited by examiner

*Primary Examiner* — Gerald R Ewoldt
*Assistant Examiner* — Marianne Dibrino
(74) *Attorney, Agent, or Firm* — Parker Highlander PLLC

(57) ABSTRACT

The present invention relates to a vaccine/inhibitor combination comprising as a vaccine at least one antigen and as an inhibitor at least one inhibitor of the major histocompatibility complex (MHC) class I restricted antigen presentation. The present invention furthermore relates to a method of vaccination of a mammal using the inventive vaccine/inhibitor combination. The present invention also provides kit of parts comprising the inventive vaccine/inhibitor combination, preferably in different parts of the kit, e.g. for prior, concurrent or subsequent administration of the different parts. Additionally the invention relates to a pharmaceutical composition comprising the inventive vaccine/inhibitor combination to further improve the immune response against tumor cells and infected cells having lost the capability of MHC class I restricted antigen presentation.

16 Claims, 5 Drawing Sheets

Figure 1:
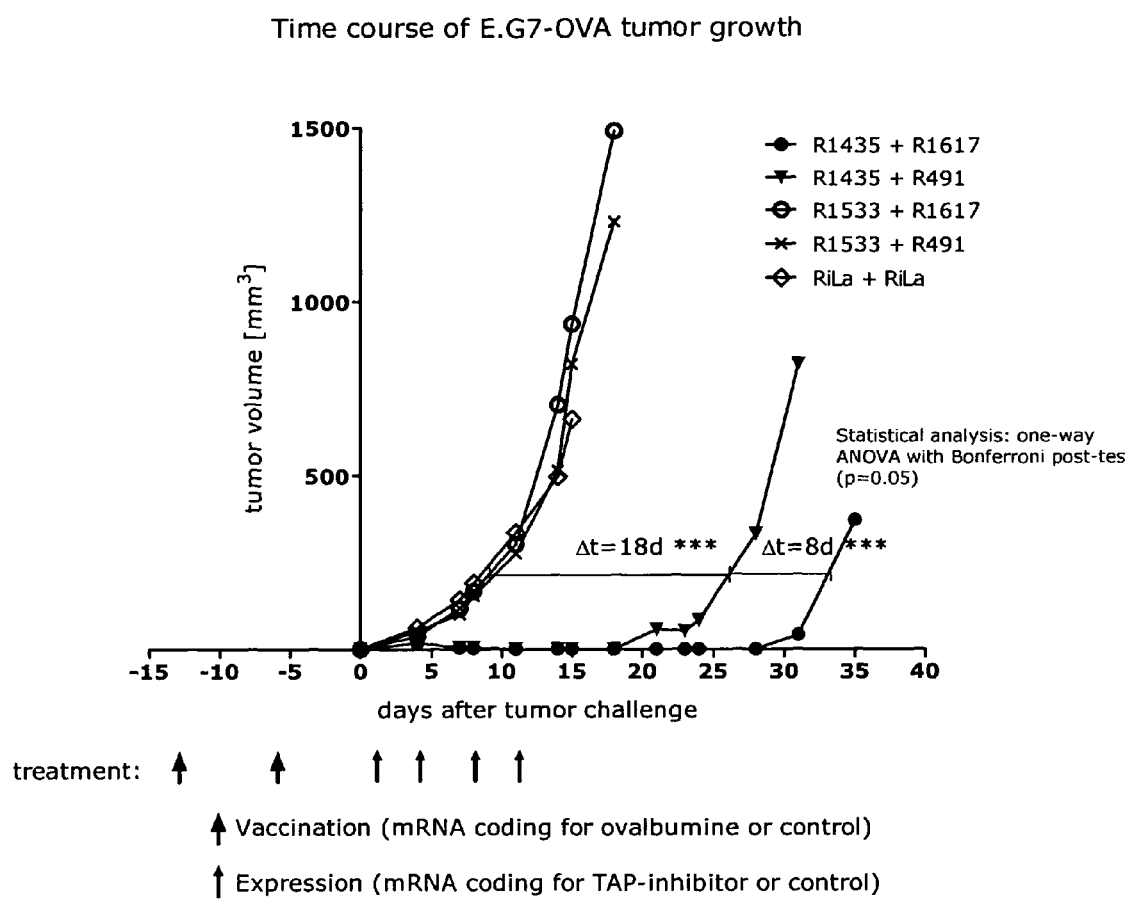

R1435:

GGGAGAAAGCUUACCAUGGGCAGCAUCGGGGCCGCGUCGAUGGAGUUCUG
CUUCGACGUGUUCAAGGAGCUGAAGGUCCACCACGCCAACGAGAACAUCU
UCUACUGCCCGAUCGCCAUCAUGAGCGCGCUCGCCAUGGUGUACCUGGGC
GCCAAGGACAGCACCCGGACGCAGAUCAACAAGGUGGUCCGCUUCGACAA
GCUGCCCGGCUUCGGGGACUCGAUCGAGGCGCAGUGCGGCACCAGCGUGA
ACGUGCACAGCUCGCUCCGGGACAUCCUGAACCAGAUCACCAAGCCGAAC
GACGUCUACAGCUUCAGCCUGGCCUCGCGGCUCUACGCCGAGGAGCGCUA
CCCGAUCCUGCCCGAGUACCUGCAGUGCGUGAAGGAGCUCUACCGGGGCG
GGCUGGAGCCGAUCAACUUCCAGACGGCGGCCGACCAGGCCCGGGAGCUG
AUCAACAGCUGGGUGGAGAGCCAGACCAACGGCAUCAUCCGCAACGUCCU
CCAGCCGUCGAGCGUGGACAGCCAGACCGCGAUGGUGCUGGUCAACGCCA
UCGUGUUCAAGGGCCUGUGGGAGAAGACGUUCAAGGACGAGGACACCCAG
GCCAUGCCCUUCCGGGUGACCGAGCAGGAGUCGAAGCCGGUCCAGAUGAU
GUACCAGAUCGGGCUCUUCCGGGUGGCGAGCAUGGCCAGCGAGAAGAUGA
AGAUCCUGGAGCUGCCGUUCGCCUCGGGCACGAUGAGCAUGCUCGUGCUG
CUGCCCGACGAGGUCAGCGGCCUCGAGCAGCUGGAGUCGAUCAUCAACUU
CGAGAAGCUGACCGAGUGGACCAGCAGCAACGUGAUGGAGGAGCGCAAGA
UCAAGGUGUACCUCCCGCGGAUGAAGAUGGAGGAGAAGUACAACCUGACG
UCGGUCCUGAUGGCGAUGGGGAUCACCGACGUGUUCAGCAGCUCGGCCAA
CCUCAGCGGCAUCAGCUCGGCCGAGAGCCUGAAGAUCAGCCAGGCGGUGC
ACGCCGCCCACGCGGAGAUCAACGAGGCCGGCCGGGAGGUCGUGGGGUCG
GCCGAGGCGGGCGUGGACGCCGCCAGCGUCAGCGAGGAGUUCCGCGCGGA
CCACCCGUUCCUGUUCUGCAUCAAGCACAUCGCCACCAACGCCGUGCUCU
UCUUCGGCCGGUGCGUGUCGCCCGACCACUAGUUAUAAGACUGACUAGC
CCGAUGGGCCUCCCAACGGGCCCUCCUCCCUCCUUGCACCGAGAUUAAU
AAAAAAAAAAAAAAAAAAAAAAAAAAAAAAAAAAAAAAAAAAAAAAAAA
AAAAAAAAAAAAAAUAUUCCCCCCCCCCCCCCCCCCCCCCCCCCCCCUC
UAG

Fig. 3

R1533/R491:
GGGAGAAAGCUUGAGGAUGGAGGACGCCAAGAACAUCAAGAAGGGCCCGG
CGCCCUUCUACCCGCUGGAGGACGGGACCGCCGGCGAGCAGCUCCACAAG
GCCAUGAAGCGGUACGCCCUGGUGCCGGGCACGAUCGCCUUCACCGACGC
CCACAUCGAGGUCGACAUCACCUACGCGGAGUACUUCGAGAUGAGCGUGC
GCCUGGCCGAGGCCAUGAAGCGGUACGGCCUGAACACCAACCACCGGAUC
GUGGUGUGCUCGGAGAACAGCCUGCAGUUCUUCAUGCCGGUGCUGGGCGC
CCUCUUCAUCGGCGUGGCCGUCGCCCCGGCGAACGACAUCUACAACGAGC
GGGAGCUGCUGAACAGCAUGGGGAUCAGCCAGCCGACCGUGGUGUUCGUG
AGCAAGAAGGGCCUGCAGAAGAUCCUGAACGUGCAGAAGAAGCUGCCCAU
CAUCCAGAAGAUCAUCAUCAUGGACAGCAAGACCGACUACCAGGGCUUCC
AGUCGAUGUACACGUUCGUGACCAGCCACCUCCCGCCGGGCUUCAACGAG
UACGACUUCGUCCCGGAGAGCUUCGACCGGGACAAGACCAUCGCCCUGAU
CAUGAACAGCAGCGGCAGCACCGGCCUGCCGAAGGGGGUGGCCCUGCCGC
ACCGGACCGCCUGCGUGCGCUUCUCGCACGCCCGGGACCCCAUCUUCGGC
AACCAGAUCAUCCCGGACACCGCCAUCCUGAGCGUGGUGCCGUUCCACCA
CGGCUUCGGCAUGUUCACGACCCUGGGCUACCUCAUCUGCGGCUUCCGGG
UGGUCCUGAUGUACCGGUUCGAGGAGGAGCUGUUCCUGCGGAGCCUGCAG
GACUACAAGAUCCAGAGCGCGCUGCUCGUGCCGACCCUGUUCAGCUUCUU
CGCCAAGAGCACCCUGAUCGACAAGUACGACCUGUCGAACCUGCACGAGA
UCGCCAGCGGGGGCGCCCCGCUGAGCAAGGAGGUGGGCGAGGCCGUGGCC
AAGCGGUUCCACCUCCCGGGCAUCCGCCAGGGCUACGGCCUGACCGAGAC
CACGAGCGCGAUCCUGAUCACCCCCGAGGGGGACGACAAGCCGGGCGCCG
UGGGCAAGGUGGUCCCGUUCUUCGAGGCCAAGGUGGUGGACCUGGACACC
GGCAAGACCCUGGGCGUGAACCAGCGGGGCGAGCUGUGCGUGCGGGGGCC
GAUGAUCAUGAGCGGCUACGUGAACAACCCGGAGGCCACCAACGCCCUCA
UCGACAAGGACGGCUGGCUGCACAGCGGCGACAUCGCCUACUGGGACGAG
GACGAGCACUUCUUCAUCGUCGACCGGCUGAAGUCGCUGAUCAAGUACAA
GGGCUACCAGGUGGCGCCGGCCGAGCUGGAGAGCAUCCUGCUCCAGCACC
CCAACAUCUUCGACGCCGGCGUGGCCGGGCUGCCGGACGACGACGCCGGC
GAGCUGCCGGCCGCGGUGGUGGUGCUGGAGCACGGCAAGACCAUGACGGA
GAAGGAGAUCGUCGACUACGUGGCCAGCCAGGUGACCACCGCCAAGAAGC
UGCGGGGCGGCGUGGUGUUCGUGGACGAGGUCCCGAAGGGCCUGACCGGG
AAGCUCGACGCCCGGAAGAUCCGCGAGAUCCUGAUCAAGGCCAAGAAGGG
CGGCAAGAUCGCCGUAAGACUAGUUAUAAGACUGACUAGCCCGAUGGG
CCUCCCAACGGGCCCUCCUCCCCUCCUUGCACCGAGAUUAAUAAAAAAA
AAAAAAAAAAAAAAAAAAAAAAAAAAAAAAAAAAAAAAAAAAAAAAAAA
AAAAAAUAUUCCCCCCCCCCCCCCCCCCCCCCCCCCCCCCUCUAG

Fig. 4

R1617:
GGGAGAAAGCUUACCAUGCCCCGGAGCCCGCUGAUCGUGGCCGUCGUGGC
CGCGGCCCUCUUCGCCAUCGUGCGCGGCCGGGACCCCCUGCUGGACGCCA
UGCGCCGGGAGGGGGCCAUGGACUUCUGGUCCGCGGGCUGCUACGCCCGC
GGGGUCCCCUCAGCGAGCCCCGCAGGCCCUGGUGGUGUUCUACGUCGC
CCUGACCGCGGUGAUGGUGGCCGUCGCCCUCUACGCCUACGGCCUGUGCU
UCCGGCUGAUGGGGGCCUCCGGCCCCAACAAGAAGGAGAGCCGCGGCCGG
GGGUGAGGACUAGUUAUAAGACUGACUAGCCCGAUGGGCCUCCCAACGGG
CCCUCCUCCCCUCCUUGCACCGAGAUUAAUAAAAAAAAAAAAAAAAAAAA
AAAAAAAAAAAAAAAAAAAAAAAAAAAAAAAAAAAAAAAAAAAUAUUCC
CCCCCCCCCCCCCCCCCCCCCCCCCUCUAG

Fig. 5

SEQUENCE LISTING

<160> NUMBER OF SEQ ID NOS: 3

<210> SEQ ID NO 1
<211> LENGTH: 1353
<212> TYPE: RNA
<213> ORGANISM: Artificial Sequence
<220> FEATURE:
<223> OTHER INFORMATION: R1435-sequence

<400> SEQUENCE: 1

| | | | | | |
|---|---|---|---|---|---|
| gggagaaagc | uuaccauggg | cagcaucggg | gccgcgucga | uggaguucug | cuucgacgug | 60 |
| uucaaggagc | ugaaggucca | ccacgccaac | gagaacaucu | cuacugccc | gaucgccauc | 120 |
| augagcgcgc | ucgccauggu | guaccugggc | gccaaggaca | gcacccggac | gcagaucaac | 180 |
| aaggugucc | gcuucgacaa | gcugcccggc | uucggggacu | cgaucgaggc | gcagugcggc | 240 |
| accagcguga | acgugcacag | cucgcuccgg | gacauccuga | accagaucac | caagccgaac | 300 |
| gacgucuaca | gcuucagccu | ggccucgcgg | cucuacgccg | aggagcgcua | cccgauccug | 360 |
| cccgaguacc | ugcagugcgu | gaaggagcuc | uaccggggcg | ggcuggagcc | gaucaacuuc | 420 |
| cagacggcgg | ccgaccaggc | ccgggagcug | aucaacagcu | ggguggagag | ccagaccaac | 480 |
| ggcaucaucc | gcaacguccu | ccagccgucg | agcguggaca | gccagaccgc | gauggugcug | 540 |
| gucaacgcca | ucguguucaa | gggccugugg | gagaagacgu | caaggacga | ggacacccag | 600 |
| gccaugcccu | uccggggugac | cgagcaggag | ucgaagccgg | uccagaugau | guaccagauc | 660 |
| gggcucuucc | gggguggcgag | cauggccagc | gagaagauga | agauccugga | gcugccguuc | 720 |
| gccucgggca | cgaugagcau | gcucgugcug | cugcccgacg | aggucagcgg | ccucgagcag | 780 |
| cuggagucga | ucaucaacuu | cgagaagcug | accgagugga | ccagcagcaa | cgugauggag | 840 |
| gagcgcaaga | ucaaggugua | ccucccgcgg | augaagaugg | aggagaagua | caaccugacg | 900 |
| ucgguccuga | uggcgauggg | gaucaccgac | guguucagca | gcucggccaa | ccucagcggc | 960 |
| aucagcucgg | ccgagagccu | gaagaucagc | caggcgguge | acgccgccca | cgcggagauc | 1020 |
| aacgaggccg | gccgggaggu | cgugggggucg | gccgaggcgg | gcguggacgc | cgccagcguc | 1080 |
| agcgaggagu | ccgcgcgga | ccacccguuc | cuguucugca | ucaagcacau | cgccaccaac | 1140 |
| gccgugcucu | ucuucggccg | gugcgugucg | cccugaccac | uaguuauaag | acugacuagc | 1200 |
| ccgaugggcc | ucccaacggg | cccuccuccc | cuccuugcac | cgagauuaau | aaaaaaaaaa | 1260 |
| aaaaaaaaaa | aaaaaaaaaa | aaaaaaaaaa | aaaaaaaaaa | aaaaaaaaaa | aaaauauucc | 1320 |
| ccccccccc | ccccccccc | cccccccuc | uag | | | 1353 |

<210> SEQ ID NO 2
<211> LENGTH: 1845
<212> TYPE: RNA
<213> ORGANISM: Artificial Sequence
<220> FEATURE:
<223> OTHER INFORMATION: R1533/R491-sequence

<400> SEQUENCE: 2

| | | | | | |
|---|---|---|---|---|---|
| gggagaaagc | uugaggaugg | aggacgccaa | gaacaucaag | aagggcccgg | cgcccuucua | 60 |
| cccgcuggag | gacgggaccg | ccggcgagca | gcuccacaag | gccaugaagc | gguacgcccu | 120 |
| ggugccgggc | acgaucgccu | ucaccgacgc | ccacaucgag | gucgacauca | ccuacgcgga | 180 |
| guacuucgag | augagcgugc | gccuggccga | ggccaugaag | cgguacggcc | ugaacaccaa | 240 |
| ccaccggauc | gugguguguu | cggagaacag | ccugcaguuc | uucaugccgg | ugcugggcgc | 300 |
| ccucuucauc | ggcguggccg | ucgccccggc | gaacgacauc | uacaacgagc | gggagcugcu | 360 |

-continued

```
gaacagcaug gggaucagcc agccgaccgu gguguucgug agcaagaagg gccugcagaa    420
gauccugaac gugcagaaga agcugcccau cauccagaag aucaucauca uggacagcaa    480
gaccgacuac cagggcuucc agucgaugua cacguucgug accagccacc ucccgccggg    540
cuucaacgag uacgacuucg ucccggagag cuucgaccgg acaagacca ucgcccugau     600 caugaacagc agcggcagca ccggccugcc gaaggggug gcccugccgc accggaccgc     660
cugcgugcgc uucucgcacg cccgggaccc caucuucggc aaccagauca ucccggacac    720
cgccauccug agcgugguge cguuccacca cggcuucggc auguucacga cccugggcua    780 ccucaucucug gcuuccggg uggucccugau guaccgguuc gaggaggagc uguuccugcg    840
gagccugcag gacuacaaga uccagagcgc gcugcucgug ccgacccugu ucagcuucuu    900
cgccaagagc acccugaucg acaaguacga ccugucgaac cugcacgaga ucgccagcgg    960
gggcgccccg cugagcaagg aggugggcga ggccgugggcc aagcgguucc accucccggg   1020
cauccgccag ggcuacggcc ugaccgagac cacgagcgcg auccugauca ccccgagggg   1080
ggacgacaag ccgggcgccg ugggcaaggu ggucccguuc uucgaggcca aggugggga    1140 ccuggacacc ggcaagaccc ugggcgugaa ccagcggggc gagcugugcg ugcggggcc    1200 gaugaucaug agcggcuacg ugaacaaccc ggaggccacc aacgcccuca ucgacaagga   1260
cggcuggcug cacagcggcg acaucgccua cugggacgag gacgagcacu ucuucaucgu   1320
cgaccggcug aagucgcuga ucaaguacaa gggcuaccag guggcgccgg ccgagcugga   1380
gagcauccug cuccagcacc ccaacaucuu cgacgccggc guggccgggc ugccggacga   1440
cgacgccggc gagcugccgg ccgcgguggu ggugcuggag cacggcaaga ccaugacgga   1500
gaaggagauc gucgacuacg uggccagcca ggugaccacc gccaagaagc ugcggggcgg   1560 cguggguuc guggacgagg ucccgaaggg ccugaccggg aagcucgacg cccggaagau    1620
ccgcgagauc cugaucaagg ccaagaaggg cggcaagauc gccguguaag acuaguuaua   1680
agacugacua gcccgauggg ccucccaacg ggccccuccu cccuccuugc accgagauua   1740
auaaaaaaaa aaaaaaaaaa aaaaaaaaaa aaaaaaaaaa aaaaaaaaaa aaaaaaaaaa   1800
aaaaauauau cccccccccc cccccccccc cccccccccc ucuag                  1845
```

<210> SEQ ID NO 3
<211> LENGTH: 483
<212> TYPE: RNA
<213> ORGANISM: Artificial Sequence
<220> FEATURE:
<223> OTHER INFORMATION: R1617-sequence

<400> SEQUENCE: 3

```
gggagaaagc uuaccaugcc ccggagcccg cugaucgugg ccgucgugc cgcggcccuc      60 uucgccaucg ugcgcggccg ggaccccug cuggacgcca ugcgccggga gggggccaug    120
gacuucuggu ccgcgggcug cuacgcccgc ggggucccc ucagcgagcc cccgcaggcc    180
cugguggugu ucuacgucgc ccugaccgcg gugaugguge ccgucgcccu cuacgccuac    240
ggccugugcu uccggcugau gggggccucc ggccccaaca agaaggagag ccgcggccgg    300
gggugaggac uaguuauaag acugacuagc ccgaugggcu uccaacggg cccuccuccc    360 cuccuugcac cgagauuaau aaaaaaaaaa aaaaaaaaaa aaaaaaaaaa aaaaaaaaaa    420
aaaaaaaaaa aaaaaaaaaa aaauauuucc cccccccccc cccccccccc cccccccccuc   480 uag                                                                   483
```

COMBINATION OF VACCINATION AND INHIBITION OF MHC CLASS I RESTRICTED ANTIGEN PRESENTATION

CROSS REFERENCE TO RELATED APPLICATIONS

This application is a U.S. National Phase filing under 35 U.S.C. §371 of International Application PCT/EP2011/006585, filed Dec. 27, 2011, and published as WO 2012/089338 on Jul. 5, 2012. PCT/EP2011/006585 claimed benefit of priority from International Application PCT/EP2010/007969, filed Dec. 29, 2010. The entire contents of each of the prior applications are hereby incorporated herein by reference. Subject matter incorporated by reference is not considered to be an alternative to any claim limitations, unless otherwise explicitly indicated.

The present invention relates to a vaccine/inhibitor combination comprising as a vaccine at least one antigen and as an inhibitor at least one inhibitor of the major histocompatibility complex (MHC) class I restricted antigen presentation. Such an inhibitor can induce expression of T cell epitopes associated with impaired peptide processing (TEIPPs) in antigen presenting cells (APCs) and thereby stimulates specific T cell mediated immune responses against cancer and pathogen infected cells which present these TEIPPs due to impairment of MHC class I restricted antigen presentation. The inventive vaccine/inhibitor combination is therefore particularly suitable in the treatment of tumour diseases and infectious diseases which are associated with loss of MHC class I restricted antigen presentation. The present invention furthermore relates to a method of vaccination of a mammal using the inventive vaccine/inhibitor combination. The present invention also provides kit of parts comprising the inventive vaccine/inhibitor combination, preferably in different parts of the kit, e.g. for prior, concurrent or subsequent administration of the different parts. Additionally the invention relates to a pharmaceutical composition comprising the inventive vaccine/inhibitor combination to further improve the immune response against tumour cells and infected cells having lost the capability of MHC class I restricted antigen presentation.

In an adaptive immune response an antigen is typically recognized by two distinct sets of highly variable receptor molecules, the immunoglobins, that serve as antigen receptors on B cells, and the antigen specific receptors of T cells. In this context peptides from the cytosol are usually bound to MHC class I molecules and recognized by CD8$^+$ T cells, whereas peptides generated in vesicles are typically bound to MHC class II molecules and recognized by CD4$^+$ T cells. Furthermore, MHC class I molecules are expressed on all nucleated cells, whereas MHC class II molecules are preferentially expressed on professional antigen presenting cells.

One main object of the immune system is to distinguish in self and non-self antigens but also into infected cells or abnormal cells. As known up to date, proteins occurring in and being produced by normal cells are continually degraded and replaced with newly synthesized proteins. In this context, much cytosolic protein degradation (including proteins of intracellular pathogens) is carried out by proteasomes. These proteasomes break the proteins into short peptides which are subsequently loaded on MHC class I molecules in the endoplasmatic reticulum (ER) by transporters associated with antigen processing (TAP). Thus, TAPs are responsible for the delivery of the cytosolic peptide repertoire resulting from proteolytic breakdown of intracellular proteins into the endoplasmic reticulum (ER), thereby making these short peptides available for loading onto MHC class I molecules.

More precisely, newly synthesized MHC class I α chains that enter the ER membranes have been found to bind to the chaperone protein calnexin, which retains the MHC class I molecule in a partially folded state in the ER. When β2-microglobulin binds to the α chain of the MHC class I molecule, a partially folded α:β2-microglobulin heterodimer is formed, which dissociates from calnexin and now binds to a complex of proteins, inter alia calreticulin and ERp57. A second component of the newly formed complex is the TAP associated protein tapasin, which forms a bridge between MHC class I molecules and TAP1 and TAP2 and allows the transport of a degraded short peptide from the cytosol. This complex is termed peptide loading complex (PLC). After binding the degraded short peptide the MHC class I molecule leaves the ER and is transported to the cell surface where it can be recognized by cytotoxic CD8$^+$ T cells (see also Parcej and Tamé, Nature Chemical Biology 6, 572-580 (2010)).

Importantly, a MHC class I epitope repertoire of normal cells does normally not induce the elimination of a cell, because the immune system has learned only to eliminate infected cells or abnormal cells with a divergent MHC class I epitope repertoire. Therefore CD8$^+$ T cells only eliminate cells which bear the epitopes on MHC class I molecules fitting in their T cell receptor and which are recognized as foreign or abnormal from the immune system. In case of an infection with an intracellular pathogen many MHC class I molecules of the cell are filled with peptides of the pathogen instead of peptides from the normal cell and thus display a different epitope repertoire on MHC class I molecules. Likewise, tumour cells show a different epitope repertoire on MHC class I molecules when compared to normal cells, at least with regard to the quantity of one or more presented epitopes. Therefore the immune system is able to specifically recognize abnormal cells (e.g. tumour cells) or infected cells by recognition of the epitopes on MHC class I molecules.

Since presentation of pathogenic peptides by MHC class I molecules signals CD8$^+$ T cells to kill the infected cell, some pathogens, in particular viruses, have evolved ways of evading recognition by preventing the appearance of peptide:MHC class I complexes at the cell surface. For instance, the herpex simplex virus prevents the transport of viral peptides into the ER by producing a protein that binds to and inhibits TAP. Meanwhile, further mechanisms have been uncovered and it appears that many steps of antigen presenting on MHC class I molecules can be inhibited to prevent recognition of infected cells by CD8$^+$ T cells. Such steps which can be inhibited in antigen presentation on MHC class I molecules include e.g.:

1. Transcriptional down-regulation of MHC class I molecules (e.g. *Mycobacterium tuberculosis*);
2. mRNA degradation of MHC class I components (e.g. vhs of Herpes simplex virus)
3. Degradation of the pre-peptide loading complex in the ER (US2 and 11 of human cytomegalovirus (HCMV));
4. Inhibition of the formation of the peptide-loading complex (PLC)
5. Retention of MHC class I molecules within the ER and prevention of PLC interactions (e.g. adenovirus gene product E19, US3, US10 and pp71 of HCMV, m152 of mouse cytomegalovirus);

a.) Degradation of PLC components (e.g. mK3 of γ-2 herpesviruses and poxviruses, UL49.5 of varicelloviruses (e.g. bovine herpesvirus 1 and pseudorabies virus), US3 of HCMV)

b.) Shutting off the crucial supply of peptide (e.g. by inhibition of TAP) (e.g. US6 of HCMV, ICP47 of herpes simplex virus, UL49.5 of varicelloviruses, BNLF2a of Epstein-Barr virus (EBV));

c.) Transit to the cell surface (e.g. U21 of herpes simplex virus);

d.) Down-regulation of cell surface molecules which induce mis-sorting or enhanced internalization of the PLC complex (e.g. K3 and K5 of Kaposi's sarcoma-associated herpesvirus, Nef of HIV, Gp48 of mCMV, HHV6 U21 proteins, BILF1 of EBV, BGLF5 and SOX of EBV);

6. Inhibition of the proteasom (e.g. bortezomib, ritonavir, disulfuram, epigallocatechin-3-gallate, galinosporamide A, calpain inhibitors, lactacystin, epoxomicin, MG-132, MG-115, MG-262);

(inter alia reviewed in Antoniou, A. N. and S. J. Powis (2008). "Pathogen evasion strategies for the major histocompatibility complex class I assembly pathway." Immunology 124(1): 1-12.). As many steps can be inhibited in antigen presentation on MHC class I molecules several investigators suggested the treatment of autoimmune diseases or transplant rejection with such inhibitors to prevent the rejection of normal cells by CD8$^+$ T cells (see e.g. WO 95/15384).

Further investigations of antigen presentation on MHC class I molecules showed that defects in MHC class I restricted antigen presentation are frequently present in human cancers and often result in escape of tumours from cytotoxic T lymphocyte (CTL) immune surveillance. In this context, different MHC class I abnormalities have been found in solid tumours of distinct origin, but also in hematopoietic diseases. These include structural alterations such as total, haplotype and allelic loss of the MHC class I heavy chain, deletions and point mutations, in particular in β2-microglobulin and TAP1 as well as dysregulation of various components of the MHC class I antigen processing machinery (APM), which could occur at the epigenetic, transcriptional and posttranscriptional level (reviewed e.g. in Seliger, B. (2008); "Molecular mechanisms of MHC class I abnormalities and APM components in human tumours." Cancer Immunol Immunother 57(11): 1719-26). The lack or downmodulation of the expression of single or multiple components of the MHC class I antigen processing pathway may avoid the recognition of tumour cells by tumour-specific CD8$^+$ cytotoxic T lymphocytes. However, it is noteworthy that the immune system has two activities. On one hand side the tumour growth could induce anti-tumour immune responses due to the presentation of tumour antigens to CD8$^+$ cytotoxic T lymphocytes (CTL). On the other hand side highly efficient immune responses could result in cancer progression due to selection of immune escape variants, which could not be recognized by immune effector cells.

This discovery led to extensive investigations to explore the mechanisms of impaired antigen presentation on MHC class I molecules. It could be shown that TAP-/- tumour cells display epitopes on MHC class I molecules which result from presentation via a TAP-independent pathway and mainly result from housekeeping genes (van Hall, T., E. Z. Wolpert, et al. (2006), "Selective cytotoxic T-lymphocyte targeting of tumour immune escape variants." Nat Med 12(4): 417-24.). These epitopes were named TEIPPs (T-cell epitopes associated with impaired peptide processing). Previously, Wolpert et al. (1997) could show for the first time that immunization with TAP-deficient cells elicits a T cell response directed against TAP-deficient tumour cells. Wolpert et al. (1997) also showed that treatment with these generated T cells can prevent growth of TAP-deficient tumour cells. Furthermore the authors suggest a vaccine consisting of TEIPPs for the treatment of cancer and virus diseases, which are associated with impaired antigen presentation on MHC class I molecules (Wolpert, E. Z., M. Petersson, et al. (1997). "Generation of CD8$^+$ T cells specific for transporter associated with antigen processing deficient cells." Proc Natl Acad Sci USA 94(21): 11496-501 and WO98/2564). Van Hall et al (2006) could show that these newly discovered epitopes can be exploited for immune intervention against processing-deficient tumours through adoptive T-cell transfer or peptide vaccination. They also suggested that in TAP-proficient tumour cells TEIPPs are out-competed by epitopes resulting from TAP-dependent presentation and therefore are not displayed in early-stage cancers. Moreover they are not presented in normal "healthy" tissue, in which the TAP-machinery usually is functional. These peptides, although derived from self antigens are not presented by normal cells. This explains why they act as immunogenic neoantigens.

It could further be shown that these newly discovered TEIPPs are presented by Qa-1b or by its human homologue human leukocyte antigen (HLA)-E, respectively, which are conserved MHC class I like molecules, often categorized as "non-classical" or class Ib MHC (Oliveira, C. C., P. A. van Veelen, et al. "The nonpolymorphic MHC Qa-1b mediates CD8$^+$ T cell surveillance of antigen-processing defects." J Exp Med, 2010, 207(1): 207-21). Similar to the classical MHC molecules, they accommodate small peptides in their binding grooves and present these on the cell surface. T cell receptor recognition of these non-classical MHCs has been described in the context of immunity against intracellular pathogens, e.g., *Listeria, Salmonella*, and *Mycobacterium tuberculosi*. Oliveira et al. (2010) furthermore described the existence of a surprisingly broad peptide repertoire that is presented by Qa-1b on cells with impairments in the antigen-processing machinery. These peptides are targeted by a unique population of CD8$^+$ cytotoxic T cells. Normal cells with intact processing machinery were not recognized by these Qa-1b restricted CTLs, but partial defects readily resulted in the appearance of the immunogenic self peptides, which are derived from housekeeping proteins. Furthermore they showed that these Qa-1b restricted T cells are abundantly present in the immune response to processing deficient tumours and suggested that identified neoantigens presented in HLA-E constitute universal epitopes that might be exploited for the therapy of frequently occurring tumour immune escape variants and persistent infections by viruses encoding immune evasion proteins.

Summarizing the above it could be shown in the prior art that pathogens, particularly viruses, exist which inhibit normal antigen presentation on MHC class I molecules. This function allows the pathogen to persist in the host for a long time without being discovered and eliminated by the immune system. In return the host, in particular humans, developed an alternative mechanism to present antigenic epitopes which are then termed T cell epitopes associated with impaired peptide processing (TEIPPs). These inhibitors were suggested as medicaments for prevention of rejection reaction against transplants and treatment of autoimmune diseases.

In further studies it could be shown that tumour escape is often associated with a loss in normal antigen presentation on MHC class I molecules. To prevent tumour escape it was suggested to generate CTLs (cytotoxic T cells) specific for TEIPPs (T cell epitopes associated with impaired peptide processing) by introducing an inhibitor of MHC class I restricted antigen presentation or to vaccinate against TEIPPs (van Hall et al. (2006), see above).

So far, a promising series of cancer vaccines has been evaluated in clinical trials. However, even though encouraging results have been presented the demonstration of a clinical benefit in confirmatory studies has been proven to be difficult. In detail, the development of cancer vaccines is hampered by a range of issues particular to this field of research. It is also well established that tumours develop 'escape mechanisms' which allow them to evade therapies based on antigen specific monovalent therapy. Furthermore it is very difficult to develop medicaments especially vaccines against pathogens which prevent antigen presentation on MHC class I molecules and therefore persist in the body for a long time, often for the whole life span.

Accordingly, it is the object of the present invention to avoid such problems, in particular to avoid or at least diminish such escape mechanisms, and thus to improve the treatment of diseases, e.g. of cancer diseases and infectious diseases, which are associated with such an impairment of antigen presentation on MHC class I molecules.

This object is solved by the subject matter of the present invention, preferably by the subject matter of the attached claims. Particularly, the present invention solves the above object by a "vaccine/inhibitor combination" comprising as a vaccine at least one antigen and as an inhibitor at least one inhibitor of the major histocompatibility complex (MHC) class I restricted antigen presentation, as well as by methods of treatments, pharmaceutical compositions and uses or kits involving such a "vaccine/inhibitor combination".

In the context of the present invention, the term "vaccine/inhibitor combination" preferably means a combined occurrence of a vaccine comprising at least one antigen and of at least one inhibitor of MHC class I restricted antigen presentation, preferably within one treatment. In other words, the administration of the vaccine and the inhibitor may occur either simultaneously or timely staggered, either at the same site of administration or at different sites of administration, as further outlined below. Such a vaccine/inhibitor combination may, on the one hand side, induce an active immune response and, on the other hand side, induce expression of T cell epitopes associated with impaired peptide processing (TEIPPs) via the inhibitor of the major histocompatibility complex (MHC) class I restricted antigen presentation. The inventive vaccine/inhibitor combination is thus suitable to effectively stimulate specific T cell mediated immune responses against cancer and pathogen infected cells. More precisely, the inventive vaccine/inhibitor combination is particularly suitable in the treatment of tumour diseases and infectious diseases which are associated with a loss of MHC class I restricted antigen presentation and to further improve the immune response against such tumour cells and infected cells.

More precisely, the inventive vaccine/inhibitor combination preferably allows eliciting a CD8$^+$ specific adaptive immune response in a patient to be treated, preferably a mammal, by using, e.g., as a first component a vaccine, which allows generation of an immune response targeting the tumour or infected cells. Addition of an inhibitor of MHC class I restricted antigen presentation then preferably induces the presentation of TEIPPs in antigen presenting cells (APCs), which can induce an elimination of those escaped tumour cells or infected cells which present the same TEIPPs as the induced APCs.

The present invention is based on the surprising finding that administration of a vaccine directed against a pathogenic or tumour antigen in combination with an inhibitor of MHC class I restricted antigen presentation could strongly decrease the harmful impact of a disease to be treated, e.g. the growth rate of a tumour. In this context the inventors surprisingly found that treatment with a vaccine comprising a tumour antigen in combination with an inhibitor of MHC class I restricted antigen presentation unexpectedly improved inhibition of tumour growth in a synergistic manner. In any case, the present invention does not require the administration of fusion proteins comprising an MHC class I chain, e.g. the MHC class I heavy chain or β2m (or nucleic acids or vectors expressing these proteins, respectively), and an epitope (or a nucleic acid or vector expressing such an epitope). Accordingly, the present invention provides antigens, which—in a preferred embodiment—do not correspond to fusion proteins (combining the antigen artificially to another protein) and, in a further preferred embodiment, do not correspond to fusion proteins comprising an MHC class I (heavy) chain or β2m fused to whatever other protein, e.g. an epitope, if a fusion protein shall be used according to the invention. Similarly, the present invention is preferably not directed to nucleic acids or vectors corresponding to such fusion proteins. Still further in another embodiment, the present invention does preferably not make use of an MHC class heavy chain or β2m as components of the inventive vaccine/inhibitor combination or composition (or nucleic acids or vectors coding for the MHC class I heavy chain or β2m). Accordingly, in such a situation, the inventive vaccine/inhibitor combination or composition does not include an MHC class I heavy chain or β2m, be it as a protein or as a nucleic acid or a vector coding for the MHC class I heavy chain or β2m.

According to the present invention the inventive combination or composition achieves the formation and presentation of TEIPPs of the antigen component itself of that inventive combination or composition. Accordingly, the antigen(s) of the inventive combination/composition is/are presented in the form of TEIPPs.

Without being bound by theory, the inventors strongly assume that infected cells or tumour cells, which show normal antigen presentation on MHC class I cells, are typically eliminated by CD8$^+$ T cells via vaccination against the pathogenic or tumour antigen. Therefore, usually a selection on tumour cells or infected cells with an impaired antigen presentation takes place and the tumour or the infected cells escape from the control of the immune system upon vaccination alone. In case of escaped tumour cells or infected cells, however, which do not show normal antigen presentation on MHC class I cells, additional treatment with an inhibitor of MHC class I restricted antigen presentation generates antigen presenting cells (APCs), which present the same epitopes (TEIPPs) as the escaped tumour cells or the infected cells. Therefore, these TEIPP specific APCs can induce a CD8$^+$ specific immune response by specifically eliminating the TEIPP presenting infected cells or tumour cells.

According to a first embodiment, the object underlying the present invention is solved by a vaccine comprising at least one antigen, preferably to be administered to a patient in need thereof, in combination with an inhibitor of the major histocompatibility complex (MHC) class I restricted antigen presentation, i.e. a vaccine/inhibitor combination.

That specific inventive combination ensures that the formation of TEIPPs of the antigen(s) (as provided by the vaccine which is a component of the inventive combination) is induced and, accordingly, these TEIPPs of the administered antigens are presented on competent immune cells of the vaccinated patient.

This inventive combination of a vaccine and an inhibitor of MHC class I restricted antigen presentation shows an extremely advantageous inhibition of tumour growth which could not be expected from the prior art. It is particularly advantageous on the one hand side to induce an adaptive immune response against tumour or infected cells by vaccination which in turn present TEIPPs on their surface to escape from the immune system and on the other hand side to generate TEIPP-specific APCs by administration of an inhibitor of MHC class I restricted antigen presentation. To ensure that these separate mechanisms are not negatively influenced by each other, the inhibitor and the vaccine are preferably administered separated in time (in a time-staggered manner) and/or are administered at different administration sites. This means that the vaccine may be administrated e.g. prior, concurrent or subsequent to the inhibitor, or vice versa. Alternatively or additionally, the vaccine and the inhibitor may be administered at different administration sites, or at the same administration site, preferably, when administered in a time staggered manner. According to a particularly preferred aspect, the vaccine is to be administered firstly and the inhibitor is to be administered subsequent to the vaccine. This procedure ensures that the selection on TEIPP expressing cells has already taken place, even though a concurrent administration or an administration, wherein the inhibitor is to be administered prior to the vaccine, may lead to the same or at least comparable results.

In the context of the present invention an inhibitor of MHC class I restricted antigen presentation is preferably defined as a compound, capable to impair antigen presentation via MHC class I molecules, e.g. inducing transcriptional down-regulation of MHC class I molecules, inducing mRNA degradation of MHC class I components, inducing degradation of the pre-peptide loading complex in the ER, inducing inhibition of the formation of the peptide-loading complex (PLC), inducing retention of MHC class I molecules within the ER and prevention of PLC interactions, inducing degradation of PLC (peptide loading complex) components, inducing shutting off the crucial supply of peptide, inducing transit of the MHC complex to the cell surface, inducing down-regulation of cell surface molecules which induce mis-sorting or enhanced internalization of the PLC complex, inducing inhibition of the proteasom, or inducing any further suitable mechanism known to a skilled person to impair antigen presentation via MHC class I molecules.

More preferably, such an inhibitor of MHC class I restricted antigen presentation includes all inhibitors which are known in the art to impair antigen presentation on MHC class I molecules according to any of the above pathways, more preferably inhibitors, which induce 1. Transcriptional down-regulation of MHC class I molecules, selected e.g. from inhibitor of *Mycobacterium tuberculosis*;
2. mRNA degradation of MHC class I components, selected e.g. from vhs of Herpes simplex virus;
3. Degradation of the pre-peptide loading complex in the ER, selected e.g. from US2 und 11 of human cytomegalovirus (HCMV);
4. Inhibition of the formation of the peptide-loading complex (PLC);
5. Retention of MHC class I molecules within the ER and prevention of PLC interactions, selected e.g. from adenovirus gene product E19, US3, US10 and pp71 of HCMV, m152 of mouse cytomegalovirus;
7. Degradation of PLC (peptide loading complex) components, selected e.g. from mK3 of γ-2 herpesviruses and poxviruses, UL49.5 of varicelloviruses (e.g. bovine herpesvirus 1 and pseudorabies virus), US3 of HCMV;
8. Shutting off the crucial supply of peptide; selected e.g. from by inhibition of TAP (e.g. US6 of HCMV, ICP47 of herpes simplex virus, UL49.5 of varicelloviruses, BNLF2a of Epstein-Barr virus (EBV));
9. Transit of the MHC complex to the cell surface, selected e.g. from U21 of herpes simplex virus;
10. Down-regulation of cell surface molecules which induce mis-sorting or enhanced internalization of the PLC complex, selected e.g. from K3 and K5 of Kaposi's sarcoma-associated herpesvirus, Nef of HIV, Gp48 of mCMV, HHV6 U21 proteins, BILF1 of EBV, BGLF5 and SOX of EBV;
11. Inhibition of the proteasom, selected e.g. from bortezomib, ritonavir, disulfuram, epigallocatechin-3-gallate, galinosporamide A, calpain inhibitors, lactacystin, epoxomicin, MG-132, MG-115, MG-262.

In this context the inhibitor of MHC class I restricted antigen presentation can be provided in form of a (recombinant) protein, as a nucleic acid coding for the inhibitor as defined herein for coding nucleic acids, or e.g. as a (small) organic molecule.

In another embodiment, the MHC class I inhibitor is not an inhibitor of TAP activity, in particular not a protein inhibitor of TAP activity (or, a nucleic acid or a vector expressing such a TAP activity inhibiting protein, respectively), in particular not a viral (protein) inhibitor of TAP (transporter) activity, more particularly not the gene product of the UL49.5 gene (e.g. bovine or human herpes virus-1), or TAP inhibiting proteins US6 and/or ICP47. In other words, any MHC class I inhibitor may be selected for the present invention provided that the MHC class I inhibitor is not an inhibitor of TAP activity, more preferably is not a protein inhibitor of TAP activity (or, a nucleic acid or vector expressing such a TAP activity inhibiting protein, respectively) and even more preferably not US6 (e.g. derived from cytomegalovirus), BNLF2a (e.g. derived from Epstein-Barr virus) and/or ICP47 (e.g. derived from Herpes Simplex virus). Furthermore, in case the protein inhibitor of TAP activity shall be provided as a nucleic acid or a vector, the vector is preferably not a mammalian cell-infecting virus vector and, more preferably, not a Sendai virus vector. In another embodiment, the MHC class I inhibitor is not provided in the form of a protein (or a nucleic acid or vector expressing a TAP activity inhibiting protein, respectively), but corresponds to other classes of compounds, e.g. small organic compounds having the function of inhibiting TAP activity.

In the context of the present invention the term "vaccination" or synonymously "inoculation" preferably means administration of one or more antigenic substances (antigens) or agents. Accordingly, in the context of the present invention, a vaccine is typically a composition comprising one or more antigenic substances (antigens) or agents suitable for administration into an organism, in particular into one or more cell(s) or tissue(s) of said organism. Administration of antigens to a subject (via the inventive vaccine/inhibitor combination), either in protein form, encoded by a nucleic acid such as an (m)RNA or in any other form suitable as vaccine, typically leads to activation of the immune system, which responds by production of antibodies to the respective antigens (humoral immunity) and particularly of immune cells, more precisely by production of cytotoxic T cells (cellular immunity by CD8$^+$ T cells) directed against the respective antigens.

In another embodiment, the present invention is not directed to the administration of (transfected or modulated) cells to the patient. In other words, the inventive vaccine/inhibitor combination does not refer to the administration, or, more specifically, injection of (ex vivo) transfected or modulated cells, in particular does not refer to the administration of ex vivo transfected or modulated immune cells, such as dendritic cells (DC), e.g. DC transfected/transduced with a TAP inhibitor, such as a viral TAP inhibitor (e.g. a protein derived from gene UL49.5, which may occur in various viruses, e.g. in herpes virus, PRV or varicellovirus). Other viral TAP inhibitors which may be excluded according to the present invention are derived from Epstein-Barr virus (e.g. lymphocryptovirus (LCV)). Accordingly, the inventive combination or composition does preferably not comprise modulated or transfected cells, in particular no transfected or modulated immune cells (e.g. antigen presenting cells), more particularly no transfected or modulated DC. By that embodiment, it becomes clear that the inventive combination/composition does preferably not correspond to a DC-based vaccine, or, more generally, does preferably not correspond to a cell-based (e.g. antigen presenting cell-based) vaccine or, more generally, the inventive combination/composition is preferably free of cells and the inventive combination/composition to be administered provides the components preferably as mRNA and/or protein, more preferably as mRNA.

Furthermore, according to the present invention, the term "antigen" refers to a substance which is recognized by the immune system and is capable of triggering an antigen-specific immune response, e.g. by formation of antibodies or antigen-specific T-cells as part of an adaptive immune response. In this context, the first step of an adaptive immune response is typically the activation of naïve antigen-specific T cells by antigen-presenting cells. This occurs in the lymphoid tissues and organs through which naïve T cells are constantly passing. The three cell types that can serve as antigen-presenting cells are dendritic cells, macrophages, and B cells. Each of these cells has a distinct function in eliciting immune responses. Tissue dendritic cells take up antigens by phagocytosis and macropinocytosis and are stimulated by infection to migrate to the local lymphoid tissue, where they differentiate into mature dendritic cells. Macrophages ingest particulate antigens such as bacteria and are induced by infectious agents to express MHC class II molecules. The unique ability of B cells to bind and internalize soluble protein antigens via their receptors may be important to induce T cells. The presentation of antigen on MHC molecules leads to activation of T cells which induces their proliferation and differentiation into armed effector T cells. The most important function of effector T cells is the killing of infected cells by CD8$^+$ cytotoxic T cells and the activation of macrophages by TH1 cells which together make up cell-mediated immunity, and the activation of B cells by both TH2 and TH1 cells to produce different classes of antibody, thus driving the humoral immune response. T cells recognize an antigen by their T cell receptors. They do not recognize and bind the antigen directly, but recognize short peptide fragments instead, e.g. short peptide fragments of pathogens' protein antigens, which are bound to MHC molecules on the surfaces of other cells.

T cells fall into two major classes that have different effector functions. The two classes are distinguished by the expression of the cell-surface proteins CD4 and CD8. These two types of T cells differ in the class of MHC molecule that they recognize. The two classes of MHC molecules—MHC class I and MHC class II molecules—differ in their structure and expression pattern on tissues of the body. CD4$^+$ T cells bind to a MHC class II molecule and CD8$^+$ T cells to a MHC class I molecule. MHC class I and MHC class II molecules have distinct distributions among cells that reflect the different effector functions of the T cells that recognize them. MHC class I molecules present peptides from pathogens, commonly viruses to CD8$^+$ T cells, which differentiate into cytotoxic T cells that are specialized to kill any cell that they specifically recognize. Almost all cells express MHC class I molecules, although the level of constitutive expression varies from one cell type to the next. But not only pathogenic peptides from viruses are presented by MHC class I molecules, also self-antigens like tumour antigens are presented by them. MHC class I molecules bind peptides from proteins degraded in the cytosol and transported in the endoplasmic reticulum. Thereby MHC class I molecules on the surface of cells infected with viruses or other cytosolic pathogens display peptides from these pathogen. The CD8$^+$ T cells that recognize MHC class I:peptide complexes are specialized to kill any cells displaying foreign peptides and so rid the body of cells infected with viruses and other cytosolic pathogens. The main function of CD4$^+$ T cells (CD4$^+$ helper T cells) that recognize MHC class II molecules is to activate other effector cells of the immune system. Thus MHC class II molecules are normally found on B lymphocytes, dendritic cells, and macrophages, cells that participate in immune responses, but not on other tissue cells. Macrophages, for example, are activated to kill the intravesicular pathogens they harbour, and B cells to secrete immunoglobulins against foreign molecules. MHC class II molecules are prevented from binding to peptides in the endoplasmic reticulum and thus MHC class II molecules bind peptides from proteins which are degraded in endosomes. They can capture peptides from pathogens that have entered the vesicular system of macrophages, or from antigens internalized by immature dendritic cells or the immunoglobulin receptors of B cells. Pathogens that accumulate in large numbers inside macrophage and dendritic cell vesicles tend to stimulate the differentiation of TH1 cells, whereas extracellular antigens tend to stimulate the production of TH2 cells. TH1 cells activate the microbicidal properties of macrophages and induce B cells to make IgG antibodies that are very effective of opsonising extracellular pathogens for ingestion by phagocytic cells, whereas TH2 cells initiate the humoral response by activating naïve B cells to secrete IgM, and induce the production of weakly opsonising antibodies such as IgG1 and IgG3 (mouse) and IgG2 and IgG4 (human) as well as IgA and IgE (mouse and human).

In the context of the present invention, antigens of the vaccine included in the herein defined inventive combination of a vaccine and an inhibitor of MHC class I restricted antigen presentation typically comprise any (protein) antigen, antigenic epitope or antigenic peptide or any nucleic acid coding for them, falling under the above definition.

One class of antigens as comprised in the herein defined inventive vaccine/inhibitor combination comprises tumour antigens. "Tumour antigens" are preferably located on the surface of the (tumour) cell. Tumour antigens may also be selected from proteins, which are overexpressed in tumour cells compared to a normal cell. Furthermore, tumour antigens also include antigens expressed in cells which are (were) not themselves (or originally not themselves) degenerated but are associated with the supposed tumour. Antigens which are connected with tumour-supplying vessels or (re)formation thereof, in particular those antigens which are associated with neovascularization, e.g. growth factors, such as VEGF, bFGF etc., are also included herein. Antigens connected with a tumour furthermore include antigens from cells or tissues, typically embedding the tumour. Further, some substances (usually proteins or peptides) are expressed in patients suffering (knowingly or notknowingly) from a cancer disease and they occur in increased concentrations in the body fluids of said patients. These substances are also referred to as "tumour antigens", even though they are not antigens in the stringent meaning of an immune response inducing substance. The class of tumour antigens can be divided further into tumour-specific antigens (TSAs) and tumour-associated-antigens (TAAs). TSAs can only be presented by tumour cells and are usually never presented by normal "healthy" cells. They typically result from a tumour specific mutation. TAAs, which are more common, are usually presented by both tumour and healthy cells. These antigens are recognized and the antigen-presenting cell can be destroyed by cytotoxic T cells. Additionally, tumour antigens can also occur on the surface of the tumour in the form of, e.g., a mutated receptor. In this case, they can be recognized by antibodies. Particular preferred tumour antigens are selected from the group consisting of 5T4, 707-AP, 9D7, AFP, AlbZIP HPG 1, alpha-5-beta-1-integrin, alpha-5-beta-6-integrin, alpha-actinin-4/m, alpha-methylacyl-coenzyme A racemase, ART-4, ARTC1/m, B7H4, BAGE-1, BCL-2, bcr/abl, beta-catenin/m, BING-4, BRCA1/m, BRCA2/m, CA 15-3/CA 27-29, CA 19-9, CA72-4, CA125, calreticulin, CAMEL, CASP-8/m, cathepsin B, cathepsin L, CD19, CD0, CD22, CD25, CDE30, CD33, CD4, CD52, CD55, CD56, CD80, CDC27/m, CDK4/m, CDKN2A/m, CEA, CLCA2, CML28, CML66, COA-1/m, coactosin-like protein, collage XXIII, COX-2, CT-9/BRD6, Cten, cyclin B1, cyclin D1, cyp-B, CYPB1, DAM-10, DAM-6, DEK-CAN, EFTUD2/m, EGFR, ELF2/m, EMMPRIN, EpCam, EphA2, EphA3, ErbB3, ETV6-AML1, EZH2, FGF-5, FN, Frau-1, G250, GAGE-1, GAGE-2, GAGE-3, GAGE-4, GAGE-5, GAGE-6, GAGE7b, GAGE-8, GDEP, GnT-V, gp100, GPC3, GPNMB/m, HAGE, HAST-2, hepsin, Her2/neu, HERV-K-MEL, HLAA*0201-R17I, HLA-A11/m, HLA-A2/m, HNE, homeobox NKX3.1, HOM-TES-14/SCP-1, HOM-TES-85, HPV-E6, HPV-E7, HSP70-2M, HST-2, hTERT, iCE, IGF-1R, IL-13Ra2, IL-2R, IL-5, immature laminin receptor, kallikrein-2, kallikrein-4, Ki67, KIAA0205, KIAA0205/m, KK-LC-1, KRas/m, LAGE-A1, LDLR-FUT, MAGE-A1, MAGE-A2, MAGE-A3, MAGE-A4, MAGE-A6, MAGE-A9, MAGE-A10, MAGE-A12, MAGE-B1, MAGE-B2, MAGE-B3, MAGE-B4, MAGE-B5, MAGE-B6, MAGE-B10, MAGE-B16, MAGE-B17, MAGE-C1, MAGE-C2, MAGE-C3, MAGE-D1, MAGE-D2, MAGE-D4, MAGE-E1, MAGE-E2, MAGE-F1, MAGE-H1, MAGEL2, mammaglobin A, MART-1/melan-A, MART-2, MART-2/m, matrix protein 22, MC1R, M-CSF, ME1/m, mesothelin, MG50/PXDN, MMP11, MN/CA IX-antigen, MRP-3, MUC-1, MUC-2, MUM-1/m, MUM-2/m, MUM-3/m, myosin class I/m, NA88-A, N-acetylglucosaminyltransferase-V, Neo-PAP, Neo-PAP/m, NFYC/m, NGEP, NMP22, NPM/ALK, N-Ras/m, NSE, NY-ESO-1, NY-ESO-B, OA1, OFA-iLRP, OGT, OGT/m, OS-9, OS-9/m, osteocalcin, osteopontin, p15, p190 minor bcr-abl, p53, p53/m, PAGE-4, PAI-1, PAI-2, PART-1, PATE, PDEF, Pim-1-Kinase, Pin-1, Pml/PARalpha, POTE, PRAME, PRDX5/m, prostein, proteinase-3, PSA, PSCA, PSGR, PSM, PSMA, PTPRK/m, RAGE-1, RBAF600/m, RHAMM/CD168, RU1, RU2, S-100, SAGE, SART-1, SART-2, SART-3, SCC, SIRT2/m, Sp17, SSX-1, SSX-2/HOM-MEL-40, SSX-4, STAMP-1, STEAP, survivin, survivin-2B, SYT-SSX-1, SYT-SSX-2, TA-90, TAG-72, TARP, TEL-AML1, TGFbeta, TGFbetaRII, TGM-4, TPI/m, TRAG-3, TRG, TRP-1, TRP-2/6b, TRP/INT2, TRP-p8, tyrosinase, UPA, VEGF, VEGFR-2/FLK-1, and WT1. Such tumour antigens preferably may be selected from the group consisting of MAGE-A1 (e.g. MAGE-A1 according to accession number M77481), MAGE-A2, MAGE-A3, MAGE-A6 (e.g. MAGE-A6 according to accession number NM_005363), MAGE-C1, MAGE-C2, melan-A (e.g. melan-A according to accession number NM_5511), GP100 (e.g. GP100 according to accession number M77348), tyrosinase (e.g. tyrosinase according to accession number NM_000372), surviving (e.g. survivin according to accession number AF077350), CEA (e.g. CEA according to accession number NM_004363), Her-2/neu (e.g. Her-2/neu according to accession number M11730), WT1 (e.g. WT1 according to accession number NM_000378), PRAME (e.g. PRAME according to accession number NM_06115), EGFRI (epidermal growth factor receptor 1) (e.g. EGFRI (epidermal growth factor receptor 1) according to accession number AF288738), MUC1, mucin-1 (e.g. mucin-1 according to accession number NM_002456), SEC61G (e.g. SEC61G according to accession number NM_14302), hTERT (e.g. hTERT accession number NM_198253), 5T4 (e.g. 5T4 according to accession number NM_006670), NY-Eso-1 (e.g. NY-Eso1 according to accession number NM_001327), TRP-2 (e.g. TRP-2 according to accession number NM_001922), STEAP, PCA, PSA, PSMA, etc.

In the context of the present invention antigens from pathogens associated with impaired antigen presentation on MHC class I molecules includes antigens from viruses like Herpes-, retro-, flavi-, arena-, and polyomaviruses including simian virus 40 (SV40), the K virus of mice, and the JC and BK viruses of humans, lymphocytic choriomeningitis virus (LCMV), Epstein-Barr virus (EBV), murine leukemia virus (MuLV), mouse mammary tumour virus (MMTV), herpes simplex virus (HSV), human T-lymphotrophic virus type 1 (HTLV-1), hepatitis B, hepatitis C virus (HCV), cytomegalovirus (CMV), human immunodeficiency virus (HIV), Kaposi's sarcoma-associated herpesvirus (KSHV), human papilloma virus, West Nile Virus, adenovirus, measles virus, Rubella virus, Varicella zoster, bovine herpesvirus 1 and pseudorabies virus, poxviruses and bacteria like mycobacteria including *Mycobacterium tuberculosis*.

Antigens as defined herein, which may be part of the vaccine of the inventive vaccine/inhibitor combination, may furthermore comprise or consist of fragments or variants of these antigens, particularly of protein or peptide antigens, wherein the fragments and/or variants may share a sequence identity with one of the aforementioned antigens of at least 70%, 80% or 85%, preferably at least 90%, more preferably at least 95% and most preferably at least 96 or even 97, 98 or 99% over the whole length of the protein or peptide antigen or its encoding nucleic acid sequence.

A "fragment" in the context of the present invention, preferably in the context of (protein or peptide) antigens as defined herein, is preferably to be understood as a truncated protein or its encoding nucleic acid, i.e. a protein which is N-terminally, C-terminally or intrasequentially truncated compared to the amino acid sequence of the original (wild type) protein or its encoding nucleic acid, respectively. Especially, fragments consisting of or comprising an antigenic epitope or their encoding nucleic acids are preferred.

Fragments of such antigens of the inventive vaccine/inhibitor combination, may additionally comprise fragments preferably consisting of or comprising a sequence having or encoding a length of about 6 to about 20 or even more (contiguous) amino acids of a (protein or peptide) antigen as defined above, e.g. fragments as processed and presented by MHC class I molecules, preferably consisting of or comprising a sequence having or encoding a length of about 8 to about 10 amino acids, e.g. 8, 9, or 10, (or even 11, or 12 amino acids), or fragments as processed and presented by MHC class II molecules, preferably consisting of or comprising a sequence having or encoding a length of about 13 or more amino acids, e.g. 13, 14, 15, 16, 17, 18, 19, 20 or 30 even more amino acids, wherein these fragments may be selected from any part of the amino acid sequence of an antigen or antigenic protein or peptide as defined herein. These fragments are typically recognized by T-cells in form of a complex consisting of the peptide fragment and an MHC molecule, i.e. the fragments are typically not recognized in their native form. These fragments are also termed as T cell epitopes.

Fragments of antigens as defined herein of the vaccine of the inventive vaccine/inhibitor combination may also comprise or consist of B cell epitopes of those antigens. B cell epitopes (also called "antigen determinants") are typically fragments located on the outer surface of (native) protein or peptide antigens as defined herein, preferably consisting of or comprising a sequence having or encoding 5 to 15 amino acids, more preferably consisting of or comprising a sequence having or encoding 5 to 12 amino acids, even more preferably consisting of or comprising a sequence having or encoding 6 to 9 amino acids, wherein the epitopes may be recognized by antibodies, i.e. in their native form.

In the context of the present invention "variants" of the at least one antigen of the vaccine or the inhibitor of the inventive vaccine/inhibitor combination, may comprise or consist of an amino acid sequence which differs from the original sequence in one or more mutation(s), such as one or more substituted, inserted and/or deleted amino acid(s), and exhibits a sequence identity of at least 60%, preferably at least 70%, more preferably at least 80%, equally more preferably at least 85%, even more preferably at least 90% and most preferably at least 97%, to the wild type amino acid sequence.

In the context of the present invention a nucleic acid coding for the inhibitor of MHC class I presentation or an antigen as defined herein and as contained in the inventive vaccine/inhibitor combination can be for instance a ssDNA, dsDNA, ssRNA, dsRNA, viral DNA, viral RNA, plasmid DNA or a messenger RNA (mRNA). It is particularly preferred that the antigen and/or the inhibitor is encoded by an mRNA.

In the context of the present invention, a messenger RNA (mRNA) is typically an RNA, which is composed of several structural elements, e.g. an optional 5'-UTR region, an upstream positioned ribosomal binding site followed by a coding region, an optional 3'-UTR region, which may be followed by a poly-A tail (and/or a poly-C-tail). The (m)RNA may occur as a mono-, di-, or even multicistronic RNA, i.e. an RNA which carries the coding sequences of one, two or more antigens or antigenic proteins or peptides or inhibitors of MHC class I restricted antigen presentation. Such coding sequences in di-, or even multicistronic mRNAs may be separated by at least one IRES sequence, e.g. as defined herein.

In addition to the above mentioned modifications of the amino acid sequence of the at least one antigen or the inhibitor, it is possible to modify the nucleic acid sequence encoding the inhibitor or the antigen (if provided as nucleic acid sequence):

According to one aspect, the nucleic acid molecule coding for the at least one antigen or the inhibitor as defined herein may be provided as a "stabilized nucleic acid", preferably as a stabilized RNA, more preferably as a RNA that is essentially resistant to in vivo degradation (e.g. by an exo- or endonuclease).

In this context, the nucleic acid molecule as defined herein may contain nucleotide analogues/modifications e.g. backbone modifications, sugar modifications or base modifications. A backbone modification in connection with the present invention is a modification in which phosphates of the backbone of the nucleotides contained in inventive nucleic acid molecule as defined herein are chemically modified. A sugar modification in connection with the present invention is a chemical modification of the sugar of the nucleotides of the inventive nucleic acid molecule as defined herein. Furthermore, a base modification in connection with the present invention is a chemical modification of the base moiety of the nucleotides of the nucleic acid molecule of the inventive nucleic acid molecule. In this context nucleotide analogues or modifications are preferably selected from nucleotide analogues which are applicable for transcription and/or translation.

According to a further aspect, the nucleic acid molecule coding for the antigen or the inhibitor of the herein defined inventive vaccine/inhibitor combination can contain a lipid modification.

The nucleic acid molecule coding for the antigen or the inhibitor of the herein defined inventive vaccine/inhibitor combination may likewise be stabilized in order to prevent degradation of the nucleic acid molecule by various approaches, particularly, when RNA or mRNA is used as a nucleic acid molecule for the inventive purpose. It is known in the art that instability and (fast) degradation of RNA in general may represent a serious problem in the application of RNA based compositions. E.g., the terminal structure is typically of critical importance particularly for an mRNA. As an example, at the 5' end of naturally occurring mRNAs there is usually a so-called "cap structure" (a modified guanosine nucleotide), and at the 3' end is typically a sequence of up to 200 adenosine nucleotides (the so-called poly-A tail).

According to another aspect, the nucleic acid molecule coding for the antigen or the inhibitor of the herein defined inventive vaccine/inhibitor combination may be modified, and thus stabilized, especially if the nucleic acid molecule is in the form of a coding nucleic acid, preferably an mRNA, by modifying the G/C content of the nucleic acid molecule, preferably of the coding region thereof.

In a particularly preferred aspect of the present invention, the G/C content of the coding region of the nucleic acid molecule, preferably of an mRNA, coding for the antigen or the inhibitor of the herein defined inventive vaccine/inhibitor combination, is modified, particularly increased, compared to the G/C content of the coding region of its particular wild type coding sequence, e.g. the unmodified mRNA. The encoded amino acid sequence of the nucleic acid sequence is preferably not modified compared to the coded amino acid sequence of the particular wild type mRNA.

Especially if the modified nucleic acid molecule coding for the antigen or the inhibitor of the herein defined inventive vaccine/inhibitor combination is in the form of an mRNA or codes for an mRNA, the coding region of the modified nucleic acid is preferably modified compared to the corresponding region of the wild type mRNA or coding sequence such that at least one codon of the wild type sequence which codes for a tRNA, which is relatively rare in the cell, is exchanged for a codon, which codes for a tRNA, which is relatively frequent in the cell and carries the same amino acid as the relatively rare tRNA. By this modification, the sequences of the nucleic acid molecule of the inventive polymeric carrier cargo complex, especially if the nucleic acid is in the form of an mRNA or codes for an mRNA, is modified such that codons for which frequently occurring tRNAs are available are inserted. In other words, according to the invention, by this modification all codons of the wild type sequence, which code for a tRNA which is relatively rare in the cell can in each case be exchanged for a codon which codes for a tRNA, which is relatively frequent in the cell and which, in each case, carries the same amino acid as the relatively rare tRNA.

In a further preferred aspect of the present invention the nucleic acid sequence coding for the antigen or the inhibitor of the inventive vaccine/inhibitor combination is associated with a vehicle, transfection or complexation agent for increasing the transfection efficiency of the nucleic acid sequence. Particularly preferred agents in this context suitable for increasing the transfection efficiency are cationic or polycationic compounds, including protamine, nucleoline, spermine or spermidine, or other cationic peptides or proteins, such as poly-L-lysine (PLL), poly-arginine, basic polypeptides, cell penetrating peptides (CPPs), including HIV-binding peptides, HIV-1 Tat (HIV), Tat-derived peptides, Penetratin, VP22 derived or analog peptides, HSV VP22 (Herpes simplex), MAP, KALA or protein transduction domains (PTDs), PpT620, prolin-rich peptides, arginine-rich peptides, lysinerich peptides, MPG-peptide(s), Pep-1, L-oligomers, Calcitonin peptide(s), Antennapedia-derived peptides (particularly from *Drosophila antennapedia*), pAntp, pIsl, FGF, Lactoferrin, Transportan, Buforin-2, Bac715-24, SynB, SynB(1), pVEC, hCT-derived peptides, SAP, or histones. Additionally, preferred cationic or polycationic proteins or peptides may be selected from the following proteins or peptides having the following total formula: $(Arg)_l$; $(Lys)_m$; $(His)_n$; $(Orn)_o$; $(Xaa)_x$, wherein l+m+n+o+x=8-15, and l, m, n or o independently of each other may be any number selected from 0, 1, 2, 3, 4, 5, 6, 7, 8, 9, 10, 11, 12, 13, 14 or 15, provided that the overall content of Arg, Lys, His and Orn represents at least 50% of all amino acids of the oligopeptide; and Xaa may be any amino acid selected from native (=naturally occurring) or non-native amino acids except of Arg, Lys, His or Orn; and x may be any number selected from o, 1, 2, 3 or 4, provided, that the overall content of Xaa does not exceed 50% of all amino acids of the oligopeptide. Particularly preferred cationic peptides in this context are e.g. $Arg_7$, $Arg_8$, $Arg_9$, $H_3R_9$, $R_9H_3$, $H_3R_9H_3$, $YSSR_9SSY$, $(RKH)_4$, $Y(RKH)_2R$, etc. Further preferred cationic or polycationic compounds, which can be used as transfection agent may include cationic polysaccharides, for example chitosan, polybrene, cationic polymers, e.g. polyethyleneimine (PEI), cationic lipids, e.g. DOTMA: [1-(2,3-sioleyloxy)propyl)]-N,N,N-trimethylammonium chloride, DMRIE, di-C14-amidine, DOTIM, SAINT, DC-Chol, BGTC, CTAP, DOPC, DODAP, DOPE: Dioleyl phosphatidylethanol-amine, DOSPA, DODAB, DOIC, DMEPC, DOGS: Dioctadecylamidoglicylspermin, DIMRI: Dimyristo-oxypropyl dimethyl hydroxyethyl ammonium bromide, DOTAP: dioleoyloxy-3-(trimethylammonio)propane, DC-6-14: O,O-ditetradecanoyl-N-α-trimethylammonioacetyl)diethanolamine chloride, CLIP1: rac-[(2,3-dioctadecyloxypropyl)(2-hydroxyethyl)]-dimethylammonium chloride, CLIP6: rac-[2(2,3-dihexadecyloxypropyloxymethyloxy)ethyl]trimethylammonium, CLIP9: rac-[2 (2,3-dihexadecyloxypropyloxysuccinyloxy)ethyl]-trimethylammonium, oligofectamine, or cationic or polycationic polymers, e.g. modified polyaminoacids, such as β-aminoacid-polymers or reversed polyamides, etc., modified polyethylenes, such as PVP (poly(N-ethyl-4-vinylpyridinium bromide)), etc., modified acrylates, such as pDMAEMA (poly(dimethylaminoethyl methylacrylate)), etc., modified Amidoamines such as pAMAM (poly(amidoamine)), etc., modified polybetaminoester (PBAE), such as diamine end modified 1,4 butanediol diacrylate-co-5-amino-1-pentanol polymers, etc., dendrimers, such as polypropylamine dendrimers or pAMAM based dendrimers, etc., polyimine(s), such as PEI: poly(ethyleneimine), poly(propyleneimine), etc., polyallylamine, sugar backbone based polymers, such as cyclodextrin based polymers, dextran based polymers, chitosan, etc., silan backbone based polymers, such as PMOXA-PDMS copolymers, etc., blockpolymers consisting of a combination of one or more cationic blocks (e.g. selected from a cationic polymer as mentioned above) and of one or more hydrophilic or hydrophobic blocks (e.g. polyethyleneglycole); etc.

In this context it is particularly preferred that the mRNA coding for the antigen contained in the vaccine of the inventive vaccine/inhibitor combination is formulated as an immunostimulatory composition comprising a) an adjuvant component, comprising or consisting of at least one (m)RNA, complexed with a cationic or polycationic compound, preferably as defined herein, and b) at least one free mRNA, encoding the antigen.

According to one further embodiment, the vaccine and the inhibitor of the inventive vaccine/inhibitor combination, both forming components of the inventive vaccine/inhibitor combination, may be formulated together or separately in the same or different compositions.

According to one preferred aspect, the vaccine and the inhibitor of the inventive vaccine/inhibitor combination may be formulated together in the same composition, preferably as a vaccine. According to one further preferred aspect, the vaccine and the inhibitor of the inventive vaccine/inhibitor combination may be formulated separately in different compositions, i.e. one composition comprising or representing a vaccine containing the at least one antigen as defined herein, and one further composition comprising the inhibitor as defined herein, the composition preferably formulated as a pharmaceutical composition. Preferably, any of the compositions comprising the vaccine or the inhibitor of the inventive vaccine/inhibitor combination, forming the components of the inventive vaccine/inhibitor combination, may be defined in the following as a "composition, comprising the vaccine and/or the inhibitor of the inventive vaccine/inhibitor combination".

In a further preferred aspect of the present invention the vaccine or the inhibitor forming the components of the inventive vaccine/inhibitor combination or a composition comprising the inhibitor and/or the vaccine may be formulated with or comprise a pharmaceutically acceptable carrier and/or vehicle. In the context of the present invention, a pharmaceutically acceptable carrier typically includes the liquid or non-liquid basis of a composition comprising the inhibitor and/or the vaccine of the inventive vaccine/inhibitor combination. If the composition is provided in liquid form, the carrier will typically be pyrogen-free water; isotonic saline or buffered (aqueous) solutions, e.g. phosphate, citrate etc. buffered solutions. The injection buffer may be hypertonic, isotonic or hypotonic with reference to the specific reference medium, i.e. the buffer may have a higher, identical or lower salt content with reference to the specific reference medium, wherein preferably such concentrations of the afore mentioned salts may be used, which do not lead to damage of cells due to osmosis or other concentration effects. Reference media are e.g. liquids occurring in "in vivo" methods, such as blood, lymph, cytosolic liquids, or other body liquids, or e.g. liquids, which may be used as reference media in "in vitro" methods, such as common buffers or liquids. Such common buffers or liquids are known to a skilled person. Ringer-Lactate solution is particularly preferred as a liquid basis if the at least one antigen comprised in the vaccine or the inhibitor of the inventive vaccine/inhibitor combination is provided as nucleic acid sequence.

However, one or more compatible solid or liquid fillers or diluents or encapsulating compounds, which are suitable for administration to a patient to be treated, may be used as well for the vaccine or the inhibitor forming the components of the inventive vaccine/inhibitor combination, or for a composition comprising the inhibitor and/or the vaccine of the inventive vaccine/inhibitor combination. The term "compatible" as used here means that these constituents of the inventive pharmaceutical composition are capable of being mixed with the inventive nucleic acid as defined herein in such a manner that no interaction occurs which would substantially reduce the pharmaceutical effectiveness of the inventive pharmaceutical composition under typical use conditions.

According to a specific aspect, the vaccine of the inventive vaccine/inhibitor combination or a composition comprising the inhibitor and the vaccine of the inventive vaccine/inhibitor combination may comprise an adjuvant. In this context, an adjuvant may be understood as any compound, which is suitable to initiate or increase an immune response of the innate immune system, i.e. a non-specific immune response. With other words, when administered, the vaccine preferably elicits an innate immune response due to the adjuvant, optionally contained therein. Preferably, such an adjuvant may be selected from an adjuvant known to a skilled person and suitable for the present case, i.e. supporting the induction of an innate immune response in a mammal, e.g. an adjuvant protein as defined above or an adjuvant as defined in the following.

Particularly preferred as adjuvants suitable for depot and delivery are cationic or polycationic compounds as defined above for nucleic acid sequences coding for the antigen or the inhibitor as vehicle, transfection or complexation agent.

According to another embodiment such an adjuvant may be selected from any adjuvant known to a skilled person and suitable for the present case, i.e. supporting the induction of an innate immune response in a mammal. Preferably, the adjuvant may be selected from the group consisting of, without being limited thereto, cationic or polycationic compounds as defined above, from chitosan, TDM, MDP, muramyl dipeptide, pluronics, alum solution, aluminium hydroxide, ADJUMER™ (polyphosphazene); aluminium phosphate gel; glucans from algae; algammulin; aluminium hydroxide gel (alum); highly protein-adsorbing aluminium hydroxide gel; low viscosity aluminium hydroxide gel; AF or SPT (emulsion of squalane (5%), Tween 80 (0.2%), PLURONIC L121™ (1.25%), phosphate-buffered saline, pH 7.4); AVRIDINE™ (propanediamine); BAY R1005™ ((N-(2-deoxy-2-L-leucylaminobD-glucopyranosyl)-N-octadecyl-dodecanoyl-amide hydroacetate); CALCITRIOL™ (1-alpha,25-dihydroxy-vitamin D3); calcium phosphate gel; CAP™ (calcium phosphate nanoparticles); cholera holotoxin, cholera-toxin-A1-protein-A-D-fragment fusion protein, sub-unit B of the cholera toxin; CRL 1005 (block copolymer P1205); cytokine-containing liposomes; DDA (dimethyldioctadecylammonium bromide); DHEA (dehydroepiandrosterone); DMPC (dimyristoylphosphatidylcholine); DMPG (dimyristoylphosphatidylglycerol); DOC/alum complex (deoxycholic acid sodium salt); Freund's complete adjuvant; Freund's incomplete adjuvant; gamma inulin; Gerbu adjuvant (mixture of: i) N-acetylglucosaminyl-(P1-4)-N-acetylmuramyl-L-alanyl-D35 glutamine (GMDP), ii) dimethyldioctadecylammonium chloride (DDA), iii) zinc-L-proline salt complex (ZnPro-8); GM-CSF); GMDP (N-acetylglucosaminyl-(b 1-4)-N-acetylmuramyl-L47 alanyl-D-isoglutamine); imiquimod (1-(2-methylpropyl)-1H-imidazo[4,5-c]quinoline-4-amine); ImmTher™ (N-acetylglucosaminyl-Nacetylmuramyl-L-Ala-D-isoGlu-L-Ala-glycerol dipalmitate); DRVs (immunoliposomes prepared from dehydration-rehydration vesicles); interferongamma; interleukin-1beta; interleukin-2; interleukin-7; interleukin-12; ISCOMS™; ISCOPREP 7.0.3.™; liposomes; LOXORIBINE™ (7-allyl-8-oxoguanosine); LT 5 oral adjuvant (E. coli labile enterotoxin-protoxin); microspheres and microparticles of any composition; MF59™; (squalePreviously presentedater emulsion); MONTANIDE ISA 51™ (purified incomplete Freund's adjuvant); MONTANIDE ISA 720™ (metabolisable oil adjuvant); MPL™ (3-Q-desacyl-4'-monophosphoryl lipid A); MTP-PE and MTP-PE liposomes ((N-acetyl-L-alanyl-D-isoglutaminyl-L-alanine-2-(1,2-dipalmitoyl-sn-glycero-3-(hydroxyphosphoryloxy)) ethylamide, monosodium salt); MURAMETIDE™ (Nac-Mur-L-Ala-D-Gln-OCH3); MURAPALMITINE™ and DMURAPALMITINE™ (Nac-Mur-L-Thr-D-isoGInsnglyceroldipalmitoyl); NAGO (neuraminidase-galactose oxidase); nanospheres or nanoparticles of any composition; NISVs (non-ionic surfactant vesicles); PLEURAN™ (☐-glucan); PLGA, PGA and PLA (homo- and co-polymers of lactic acid and glycolic acid; microspheres/nanospheres); PLURONIC L121™; PMMA (polymethylmethacrylate); PODDS™ (proteinoid microspheres); polyethylene carbamate derivatives; poly-rA: poly-rU (polyadenylic acid-polyuridylic acid complex); polysorbate 80 (Tween 80); protein cochleates (Avanti Polar Lipids, Inc., Alabaster, Ala.); STIMULON™ (QS-21); Quil-A (Quil-A saponin); S-28463 (4-amino-otec-dimethyl-2-ethoxymethyl-1H-imidazo[4,5-c]quinoline-1-ethanol); SAF-1™ ("Syntex adjuvant formulation"); Sendai proteoliposomes and Sendaicontaining lipid matrices; Span-85 (sorbitan trioleate); Specol (emulsion of Marcol 52, Span 85 and Tween 85); squalene or Robane® (2,6,10,15,19,23-hexamethyltetracosan and 2,6,10,15,19,23-hexamethyl-2,6,10,14,18,22-tetracosahexane); stearyltyrosine (octadecyltyrosine hydrochloride); Theramid® (N-acetylglucosaminyl-N-acetylmuramyl-L-Ala-D-isoGlu-LAladipalmitoxypropylamide); Theronyl-MDP (Termurtide™ or [thr 1]-MDP; N-acetylmuramylLthreonyl-D-isoglutamine); Ty particles (Ty-VLPs or virus-like particles); Walter-Reed liposomes (liposomes containing lipid A adsorbed on aluminium hydroxide), and lipopeptides, including Pam3Cys, in particular aluminium salts, such as Adju-phos, Alhydrogel, Rehydragel; emulsions, including CFA, SAF, IFA, MF59, Provax, TiterMax, Montanide, Vaxfectin; copolymers, including Optivax (CRL1005), L121, Poloaxmer4010), etc.; liposomes, including Stealth, cochleates, including BIORAL; plant derived adjuvants, including QS21, Quil A, Iscomatrix, ISCOM; adjuvants suitable for costimulation including Tomatine, biopolymers, including PLG, PMM, Inulin, microbe derived adjuvants, including Romurtide, DETOX, MPL, CWS, Mannose, CpG nucleic acid sequences, CpG7909, ligands of human TLR 1-10, ligands of murine TLR 1-13, ISS-1018, IC31, Imidazoquinolines, Ampligen, Ribi529, IMOxine, IRIVs, VLPs, cholera toxin, heat-labile toxin, Pam3Cys, Flagellin, GPI anchor, LNFPIII/Lewis X, antimicrobial peptides, UC-1V150, RSV fusion protein, cdiGMP; and adjuvants suitable as antagonists including CGRP neuropeptide.

The vaccine of the inventive vaccine/inhibitor combination or a composition comprising the inhibitor and the vaccine of the inventive vaccine/inhibitor combination can additionally contain one or more auxiliary substances in order to increase its immunogenicity or immunostimulatory capacity, if desired. A synergistic action of the vaccine or an inhibitor as defined herein and of an auxiliary substance, which may be optionally contained in the vaccine or may be formulated with the inhibitor, is preferably achieved thereby. Depending on the various types of auxiliary substances, various mechanisms can come into consideration in this respect. For example, compounds that permit the maturation of dendritic cells (DCs), for example lipopolysaccharides, TNF-alpha or CD40 ligand, form a first class of suitable auxiliary substances. In general, it is possible to use as auxiliary substance any agent that influences the immune system in the manner of a "danger signal" (LPS, GP96, etc.) or cytokines, such as GM-CFS, which allow an immune response to be enhanced and/or influenced in a targeted manner. Particularly preferred auxiliary substances are cytokines, such as monokines, lymphokines, interleukins or chemokines, that further promote the innate immune response, such as IL-1, IL-2, IL-3, IL-4, IL-5, IL-6, IL-7, IL-8, IL-9, IL-10, IL-12, IL-13, IL-14, IL-15, IL-16, IL-17, IL-18, IL-19, IL-20, IL-21, IL-22, IL-23, IL-24, IL-25, IL-26, IL-27, IL-28, IL-29, IL-30, IL-31, IL-32, IL-33, IFN-alpha, IFN-beta, IFN-gamma, GM-CSF, G-CSF, M-CSF, LT-beta or TNF-alpha, growth factors, such as hGH.

The vaccine of the inventive vaccine/inhibitor combination or a composition comprising the inhibitor and the vaccine of the inventive vaccine/inhibitor combination can also additionally contain any further compound, which is known to be immunostimulating due to its binding affinity (as ligands) to human Toll-like receptors TLR1, TLR2, TLR3, TLR4, TLR5, TLR6, TLR7, TLR8, TLR9, TLR10, or due to its binding affinity (as ligands) to murine Toll-like receptors TLR1, TLR2, TLR3, TLR4, TLR5, TLR6, TLR7, TLR8, TLR9, TLR10, TLR11, TLR12 or TLR13.

In this context especially preferred as immunostimulating compounds are immunostimulatory nucleic acids which are known to bind to TLR receptors. Such an immunostimulatory nucleic acid can be in the form of a(n) (immunostimulatory) CpG nucleic acid, in particular CpG-RNA or CpG-DNA, which preferably induces an innate immune response. A CpG-RNA or CpG-DNA used according to the invention can be a single-stranded CpG-DNA (ss CpG-DNA), a double-stranded CpG-DNA (dsDNA), a single-stranded CpG-RNA (ss CpG-RNA) or a double-stranded CpG-RNA (ds CpG-RNA). The CpG nucleic acid used according to the invention is preferably in the form of CpG-RNA, more preferably in the form of single-stranded CpG-RNA (ss CpG-RNA). Also preferably, such CpG nucleic acids have a length as described above. Preferably the CpG motifs are unmethylated.

Furthermore, an immunostimulatory nucleic acid as defined above may be in the form of an immunostimulatory RNA (is RNA), which preferably elicits an innate immune response. Such an immunostimulatory RNA may be any (double-stranded or single-stranded) RNA, e.g. a coding RNA, as defined herein. Preferably, the immunostimulatory RNA may be a single-stranded, a double-stranded or a partially double-stranded RNA, more preferably a single-stranded RNA, and/or a circular or linear RNA, more preferably a linear RNA. More preferably, the immunostimulatory RNA may be a (linear) single-stranded RNA. Even more preferably, the immunostimulatory RNA may be a (long) (linear) single-stranded) non-coding RNA. In this context it is particular preferred that the is RNA carries a triphosphate at its 5'-end which is the case for in vitro transcribed RNA. An immunostimulatory RNA may also occur as a short RNA oligonucleotide as defined herein. An immunostimulatory RNA as used herein may furthermore be selected from any class of RNA molecules, found in nature or being prepared synthetically, and which can induce an innate immune response and may support an adaptive immune response induced by an antigen. In this context, an immune response may occur in various ways. A substantial factor for a suitable (adaptive) immune response is the stimulation of different T-cell sub-populations. T-lymphocytes are typically divided into two sub-populations, the T-helper 1 (Th1) cells and the T-helper 2 (Th2) cells, with which the immune system is capable of destroying intracellular (Th1) and extracellular (Th2) pathogens (e.g. antigens). The two Th cell populations differ in the pattern of the effector proteins (cytokines) produced by them. Thus, Th1 cells assist the cellular immune response by activation of macrophages and cytotoxic T-cells. Th2 cells, on the other hand, promote the humoral immune response by stimulation of B-cells for conversion into plasma cells and by formation of antibodies (e.g. against antigens). The Th1/Th2 ratio is therefore of great importance in the induction and maintenance of an adaptive immune response. In connection with the present invention, the Th1/Th2 ratio of the (adaptive) immune response is preferably shifted in the direction towards the cellular response (Th1 response) and a cellular immune response is thereby induced. According to one example, the innate immune system which may support an adaptive immune response, may be activated by ligands of Toll-like receptors (TLRs). TLRs are a family of highly conserved pattern recognition receptor (PRR) polypeptides that recognize pathogen-associated molecular patterns (PAMPs) and play a critical role in innate immunity in mammals. Currently at least thirteen family members, designated TLR1-TLR13 (Toll-like receptors: TLR1, TLR2, TLR1, TLR4, TLR5, TLR6, TLR7, TLR8, TLR9, TLR10, TLR11, TLR12 or TLR13), have been identified. Furthermore, a number of specific TLR ligands have been identified. It was e.g. found that unmethylated bacterial DNA and synthetic analogs thereof (CpG DNA) are ligands for TLR9 (Hemmi H et al. (2000) Nature 408:740-5; Bauer S et al. (2001) Proc Natl. Acad. Sci. USA 98, 9237-42). Furthermore, it has been reported that ligands for certain TLRs include certain nucleic acid molecules and that certain types of RNA are immunostimulatory in a sequence-independent or sequence-dependent manner, wherein these various immunostimulatory RNAs may e.g. stimulate TLR3, TLR7, or TLR8, or intracellular receptors such as RIG-I, MDA-5, etc. E.g. Lipford et al. determined certain G,U-containing oligoribonucleotides as immunostimulatory by acting via TLR7 and TLR8 (see WO 03/086280). The immunostimulatory G,U-containing oligoribonucleotides described by Lipford et al. were believed to be derivable from RNA sources including ribosomal RNA, transfer RNA, messenger RNA, and viral RNA.

The immunostimulatory RNA (is RNA), used as a further compound of the vaccine of the inventive vaccine/inhibitor combination or a composition comprising the inhibitor and the vaccine of the inventive vaccine/inhibitor combination, may thus comprise any RNA sequence known to be immunostimulatory, including, without being limited thereto, RNA sequences representing and/or encoding ligands of TLRs, preferably selected from human family members TLR1-TLR10 or murine family members TLR1-TLR13, more preferably selected from (human) family members TLR1-TLR10, even more preferably from TLR7 and TLR8, ligands for intracellular receptors for RNA (such as RIG-I or MDA-5, etc.) (see e.g. Meylan, E., Tschopp, J. (2006). Toll-like receptors and RNA helicases: two parallel ways to trigger antiviral responses. Mol. Cell. 22, 561-569), or any other immunostimulatory RNA sequence. Furthermore, (classes of) immunostimulatory RNA molecules, used as a further compound of the vaccine of the inventive vaccine/inhibitor combination or a composition comprising the inhibitor and the vaccine of the inventive vaccine/inhibitor combination, may include any other RNA capable of eliciting an immune response. Without being limited thereto, such an immunostimulatory RNA may include ribosomal RNA (rRNA), transfer RNA (tRNA), messenger RNA (mRNA), and viral RNA (vRNA). Such an immunostimulatory RNA may comprise a length of 1000 to 5000, of 500 to 5000, of 5 to 5000, or of 5 to 1000, 5 to 500, 5 to 250, of 5 to 100, of 5 to 50 or of 5 to 30 nucleotides.

According to a particularly preferred embodiment, such immunostimulatory nucleic acid sequences, particularly is RNA, consist of or comprise a nucleic acid of formula (I) or (II):

$$G_l X_m G_n,\qquad \text{(formula (I))}$$

wherein:
G is guanosine, uracil or an analogue of guanosine or uracil;
X is guanosine, uracil, adenosine, thymidine, cytosine or an analogue of the above-mentioned nucleotides;
l is an integer from 1 to 40,
  wherein
  when l=1 G is guanosine or an analogue thereof,
  when l>1 at least 50% of the nucleotides are guanosine or an analogue thereof;
m is an integer and is at least 3;
  wherein
  when m=3 X is uracil or an analogue thereof,
  when m>3 at least 3 successive uracils or analogues of uracil occur;
n is an integer from 1 to 40,
  wherein
  when n=1 G is guanosine or an analogue thereof,
  when n>1 at least 50% of the nucleotides are guanosine or an analogue thereof.

$$C_l X_m C_n,\qquad \text{(formula (II))}$$

wherein:
C is cytosine, uracil or an analogue of cytosine or uracil;
X is guanosine, uracil, adenosine, thymidine, cytosine or an analogue of the above-mentioned nucleotides;
l is an integer from 1 to 40,
  wherein
  when l=1 C is cytosine or an analogue thereof,
  when l>1 at least 50% of the nucleotides are cytosine or an analogue thereof;
m is an integer and is at least 3;
  wherein
  when m=3 X is uracil or an analogue thereof,
  when m>3 at least 3 successive uracils or analogues of uracil occur;
n is an integer from 1 to 40,
  wherein
  when n=1 C is cytosine or an analogue thereof,
  when n>1 at least 50% of the nucleotides are cytosine or an analogue thereof.

According to a further particularly preferred embodiment, such immunostimulatory nucleic acid sequences, particularly is RNA, consist of or comprise a nucleic acid of formula (III) or (IV):

$$(N_u G_l X_m G_n N_v)_a,\qquad \text{(formula (III))}$$

wherein:
G is guanosine (guanine), uridine (uracil) or an analogue of guanosine (guanine) or uridine (uracil), preferably guanosine (guanine) or an analogue thereof;
X is guanosine (guanine), uridine (uracil), adenosine (adenine), thymidine (thymine), cytidine (cytosine), or an analogue of these nucleotides (nucleosides), preferably uridine (uracil) or an analogue thereof;
N is a nucleic acid sequence having a length of about 4 to 50, preferably of about 4 to 40, more preferably of about 4 to 30 or 4 to 20 nucleic acids, each N independently being selected from guanosine (guanine), uridine (uracil), adenosine (adenine), thymidine (thymine), cytidine (cytosine) or an analogue of these nucleotides (nucleosides);
a is an integer from 1 to 20, preferably from 1 to 15, most preferably from 1 to 10;
l is an integer from 1 to 40,
  wherein
  when l=1, G is guanosine (guanine) or an analogue thereof,
  when l>1, at least 50% of these nucleotides (nucleosides) are guanosine (guanine) or an analogue thereof;
m is an integer and is at least 3;
  wherein
  when m=3, X is uridine (uracil) or an analogue thereof, and
  when m>3, at least 3 successive uridines (uracils) or analogues of uridine (uracil) occur;
n is an integer from 1 to 40,
  wherein
  when n=1, G is guanosine (guanine) or an analogue thereof,
  when n>1, at least 50% of these nucleotides (nucleosides) are guanosine (guanine) or an analogue thereof;
u,v may be independently from each other an integer from 0 to 50,
  preferably wherein when u=0, v≥1, or
  when v=0, u≥1;
wherein the nucleic acid molecule of formula (III) has a length of at least 50 nucleotides, preferably of at least 100 nucleotides, more preferably of at least 150 nucleotides, even more preferably of at least 200 nucleotides and most preferably of at least 250 nucleotides.

$$(N_u C_l X_m C_n N_v)_a\qquad \text{(formula (IV))}$$

wherein:
C is cytidine (cytosine), uridine (uracil) or an analogue of cytidine (cytosine) or uridine (uracil), preferably cytidine (cytosine) or an analogue thereof;
X is guanosine (guanine), uridine (uracil), adenosine (adenine), thymidine (thymine), cytidine (cytosine) or an analogue of the above-mentioned nucleotides (nucleosides), preferably uridine (uracil) or an analogue thereof;
N is each a nucleic acid sequence having independent from each other a length of about 4 to 50, preferably of about 4 to 40, more preferably of about 4 to 30 or 4 to 20 nucleic acids, each N independently being selected from guanosine (guanine), uridine (uracil), adenosine (adenine), thymidine (thymine), cytidine (cytosine) or an analogue of these nucleotides (nucleosides);

a is an integer from 1 to 20, preferably from 1 to 15, most preferably from 1 to 10;

l is an integer from 1 to 40,
  wherein
  when l=1, C is cytidine (cytosine) or an analogue thereof,
  when l>1, at least 50% of these nucleotides (nucleosides) are cytidine (cytosine) or an analogue thereof;

m is an integer and is at least 3;
  wherein
  when m=3, X is uridine (uracil) or an analogue thereof,
  when m>3, at least 3 successive uridines (uracils) or analogues of uridine (uracil) occur;

n is an integer from 1 to 40,
  wherein
  when n=1, C is cytidine (cytosine) or an analogue thereof,
  when n>1, at least 50% of these nucleotides (nucleosides) are cytidine (cytosine) or an analogue thereof.

u, v may be independently from each other an integer from 0 to 50,
  preferably wherein when u=0, v≥1, or
  when v=0, u≥1;

wherein the nucleic acid molecule of formula (IV) according to the invention has a length of at least 50 nucleotides, preferably of at least 100 nucleotides, more preferably of at least 150 nucleotides, even more preferably of at least 200 nucleotides and most preferably of at least 250 nucleotides.

For formula (III), any of the definitions given above for elements N (i.e. $N_u$ and $N_v$) and X ($X_m$), particularly the core structure as defined above, as well as for integers a, l, m, n, u and v, similarly apply to elements of formula (IV) correspondingly, wherein in formula (IV) the core structure is defined by $C_l X_m C_n$. The definition of bordering elements $N_u$ and $N_v$ is identical to the definitions given above for $N_u$ and $N_v$.

Further additives which may be included in the vaccine and/or the inhibitor of the inventive vaccine/inhibitor combination are emulsifiers, such as, for example, Tween®; wetting agents, such as, for example, sodium lauryl sulfate; colouring agents; taste-imparting agents, pharmaceutical carriers; tablet-forming agents; stabilizers; antioxidants; preservatives.

The vaccine and/or the inhibitor of the inventive vaccine/inhibitor combination may be administered orally, parenterally, by inhalation spray, topically, rectally, nasally, buccally, vaginally or via an implanted reservoir. The term parenteral as used herein includes subcutaneous, intravenous, intramuscular, intra-articular, intra-synovial, intrasternal, intrathecal, intrahepatic, intralesional, intracranial, transdermal, intradermal, intrapulmonal, intraperitoneal, intracardial, intraarterial, and sublingual injection or infusion techniques.

Preferably, the vaccine and/or the inhibitor of the inventive vaccine/inhibitor combination are administered intradermally to reach APCs in the dermis.

The vaccine and/or the inhibitor of the inventive vaccine/inhibitor combination as defined herein may also be administered orally in any orally acceptable dosage form including, but not limited to, capsules, tablets, aqueous suspensions or solutions.

The vaccine and/or the inhibitor of the inventive vaccine/inhibitor combination may also be administered topically, especially when the target of treatment includes areas or organs readily accessible by topical application, e.g. including diseases of the skin or of any other accessible epithelial tissue. Suitable topical formulations are readily prepared for each of these areas or organs. For topical applications, the vaccine and/or the inhibitor of the inventive vaccine/inhibitor combination may be formulated in a suitable ointment, containing the vaccine and/or the inhibitor and optionally further compounds as defined herein suspended or dissolved in one or more carriers.

The vaccine and/or the inhibitor typically comprise a "safe and effective amount" of the components of the inventive vaccine/inhibitor combination. As used herein, a "safe and effective amount" preferably means an amount of the vaccine and/or the inhibitor of the inventive vaccine/inhibitor combination as defined herein that is sufficient to significantly induce a positive modification of a disease or disorder as defined herein. At the same time, however, a "safe and effective amount" is small enough to avoid serious side-effects and to permit a sensible relationship between advantage and risk. The determination of these limits typically lies within the scope of sensible medical judgment.

According to a further embodiment, the object underlying the present invention is solved by a pharmaceutical composition comprising, in one or more compositions (e.g. as a kit or as a kit of parts), a vaccine comprising at least one antigen and/or an inhibitor of MHC class I restricted antigen presentation, both preferably as defined above. Likewise, the pharmaceutical composition is preferably formulated and administered as defined above for the components of the inventive vaccine/inhibitor combination.

Accordingly, the combination of the vaccine and the inhibitor of MHC class I restricted antigen presentation as defined according to the present invention in the inventive pharmaceutical composition, or in any further application as defined herein, may occur either as one composition, e.g. as a kit, comprising all these components in one and the same mixture, or may occur in more than one compositions, e.g. as a kit of parts, wherein the different components form different parts of such kit of parts. These different components may be formulated each as a vaccine, a pharmaceutical composition or as a composition as defined above. Preferably, each of the different parts of the kit comprises a different component, e.g. on part comprising the vaccine as defined herein, one further part comprising the inhibitor of MHC class I restricted antigen presentation as defined herein, etc. Such a pharmaceutical composition, as defined above, either formulated as a kit or as a kit of parts, may further comprise any ingredient as defined above for the inventive vaccine/inhibitor combination.

In the context of the present invention, the TEIPP-specific $CD8^+$-mediated immune response utilizing the inventive vaccine/inhibitor combination, preferably if in form of more than one pharmaceutical composition, may be additionally improved by an additional vaccine added to the pharmaceutical composition(s) containing the inhibitor as described herein. Such an effect is possible, because TEIPPs of the antigen(s) contained in the vaccine can be presented by the APCs additionally to the TEIPPs of housekeeping genes and increase the probability that tumour cells or infected cells which express the antigen(s) and present TEIPPs generated from these antigens are recognized and eliminated by the immune system.

Accordingly, it is particularly preferred that the inventive vaccine/inhibitor combination is combined with an additional vaccine. In this context, it may be preferred that the inventive vaccine/inhibitor combination may be formulated as two separated compositions as defined above, wherein a first composition preferably comprises the vaccine as defined above of the inventive vaccine/inhibitor combination and the second composition preferably comprises the inhibitor of the inventive vaccine/inhibitor combination and preferably an additional vaccine. Likewise, this second pharmaceutical composition may also be split into two separate compositions. These compositions are preferably prepared as defined above, e.g. for pharmaceutical compositions. Preferably, the inhibitor and the additional vaccine (forming the second composition) are to be administered at the same time and/or the same administration site to ensure that the inhibitor and the additional vaccine reach the same cells. Accordingly, it is preferred that the inhibitor and the additional vaccine, either as one composition or in form of two separate compositions, may be administered at the same time and/or the same administration site. Such an additional vaccine may as defined above for the vaccine of inventive vaccine/inhibitor combination. In this context it is preferred that the first composition and the second composition are preferably administered separated in time or locally separated similar as already outlined above for the inventive vaccine/inhibitor combination alone. The second composition comprising the inhibitor and the additional vaccine (either as one composition or in form of two separate compositions) may be administered, e.g. prior, concurrent or subsequent to the first composition, comprising the vaccine of the inventive vaccine/inhibitor combination, or vice versa. Alternatively or additionally, the first composition and the second composition (either as one or as two separate compositions) may be administered at different administration sites, or at the same administration site, preferably, when administered in a time staggered manner.

In this context it is particularly preferred to administer firstly the first composition comprising the vaccine of the inventive vaccine/inhibitor combination and subsequently a second composition as defined above comprising the inhibitor of the inventive vaccine/inhibitor combination and optional the additional vaccine (either as one or as two separate compositions) to induce an immune response against escaped tumour cells or infected cells which have lost presentation of antigen epitopes on MHC class I molecules.

The inventive vaccine/inhibitor combination or the inventive pharmaceutical composition comprising a vaccine and an inhibitor and optionally an additional vaccine (preferably in form of a first and a second composition as described above) may be used for human and also for veterinary medical purposes, preferably for human medical purposes.

According to one further specific embodiment, the present invention is directed to the first medical use of the inventive vaccine/inhibitor combination or the inventive pharmaceutical composition and optionally of an additional vaccine as defined herein (preferably in form of a first and a second composition as described above) as a medicament.

According to another embodiment, the present invention is directed to the second medical use of the inventive vaccine/inhibitor combination or the inventive pharmaceutical composition and optionally an additional vaccine as defined herein (preferably in form of a first and a second composition as described above), for the treatment of diseases as defined herein, or of kits comprising same for the preparation of a medicament for the treatment and/or amelioration of various diseases as defined herein.

Preferably, diseases as mentioned herein are selected from cancer or tumour diseases and infectious diseases, which are associated with a loss in MHC class I restricted antigen presentation.

Cancer or tumour diseases as mentioned above preferably include e.g. colon carcinomas, melanomas, renal carcinomas, lymphomas, acute myeloid leukaemia (AML), acute lymphoid leukaemia (ALL), chronic myeloid leukaemia (CML), chronic lymphocytic leukaemia (CLL), gastrointestinal tumours, pulmonary carcinomas, gliomas, thyroid tumours, mammary carcinomas, prostate tumours, hepatomas, various virus-induced tumours such as, for example, papilloma virus-induced carcinomas (e.g. cervical carcinoma), adenocarcinomas, herpes virus-induced tumours (e.g. Burkitt's lymphoma, EBVinduced B-cell lymphoma), hepatitis B-induced tumours (hepatocell carcinoma), HTLV-1- and HTLV-2-induced lymphomas, acoustic neuromas/neurinomas, cervical cancer, lung cancer, pharyngeal cancer, anal carcinomas, glioblastomas, lymphomas, rectal carcinomas, astrocytomas, brain tumours, stomach cancer, retinoblastomas, basaliomas, brain metastases, medulloblastomas, vaginal cancer, pancreatic cancer, testicular cancer, melanomas, thyroidal carcinomas, bladder cancer, Hodgkin's syndrome, meningiomas, Schneeberger disease, bronchial carcinomas, hypophysis tumour, Mycosis fungoides, oesophageal cancer, breast cancer, carcinoids, neurinomas, spinaliomas, Burkitt's lymphomas, laryngeal cancer, renal cancer, thymomas, corpus carcinomas, bone cancer, non-Hodgkin's lymphomas, urethral cancer, CUP syndrome, head/neck tumours, oligodendrogliomas, vulval cancer, intestinal cancer, colon carcinomas, oesophageal carcinomas, wart involvement, tumours of the small intestine, craniopharyngeomas, ovarian carcinomas, soft tissue tumours/sarcomas, ovarian cancer, liver cancer, pancreatic carcinomas, cervical carcinomas, endometrial carcinomas, liver metastases, penile cancer, tongue cancer, gall bladder cancer, leukaemia, plasmocytomas, uterine cancer, lid tumour, prostate cancer, etc.

Infectious diseases as mentioned above, preferably includes diseases caused by viruses like Herpes-, retro-, flavi-, arena-, and polyomaviruses including simian virus 40 (SV40), the K virus of mice, and the JC and BK viruses of humans, lymphocytic choriomeningitis virus (LCMV), Epstein-Barr virus (EBV), murine leukemia virus (MuLV), mouse mammary tumour virus (MMTV), herpes simplex virus (HSV), human T-lymphotrophic virus type 1 (HTLV-1), hepatitis B, hepatitis C virus (HCV), cytomegalovirus (CMV), human immunodeficiency virus (HIV), Kaposi's sarcoma-associated herpesvirus (KSHV), human papilloma virus, West Nile Virus, adenovirus, measles virus, Rubella virus, Varicella zoster, bovine herpesvirus 1 and pseudorabies virus, poxviruses and bacteria like mycobacteria including *Mycobacterium tuberculosis*.

According to a final embodiment, the present invention also provides kits, particularly kits of parts, as already defined herein in the context of pharmaceutical compositions. Such kits, particularly kits of parts, typically comprise as components alone or in combination with further components as defined herein at least one vaccine comprising at least one antigen and, probably in a different part of the kit, at least one inhibitor of MHC class I restricted antigen presentation as defined herein, and/or the inventive pharmaceutical composition or vaccine comprising the inventive vaccine/inhibitor combination. The inventive vaccine/inhibitor combination as defined herein, optionally in combination with further components as defined herein, such as an additional vaccine (preferably in form of a first and a second composition as described above), etc., and/or the inventive pharmaceutical composition (likewise preferably in form of a first and a second composition as described above) may occur in one or different parts of the kit. As an example, e.g.

at least one part of the kit may comprise at least one vaccine as defined herein, at least one further part of the kit at least one inhibitor of MHC class I restricted antigen presentation as defined herein, and optionally at least one further part of the kit an additional vaccine as described herein. The kit or kit of parts may furthermore contain technical instructions with information on the administration and dosage of the inventive vaccine/inhibitor combination, the inventive pharmaceutical composition or of any of its components or parts, e.g. if the kit is prepared as a kit of parts.

In the present invention, if not otherwise indicated, different features of alternatives and embodiments may be combined with each other. Furthermore, the term "comprising" shall not be construed as meaning "consisting of", if not specifically mentioned. However, in the context of the present invention, term "comprising" may be substituted with the term "consisting of", where applicable.

FIGURES

The figures shown in the following are merely illustrative and shall describe the present invention in a further way. These figures shall not be construed to limit the present invention thereto.

FIG. 1: shows the effect of the combination of vaccination against the tumour antigen ovalbumine and the administration of the TAP-Inhibitor UL49.5 on E.G7-OVA tumour growth. As can be seen as result is that expression of the TAP inhibitor alone has no effect on tumour growth, but vaccination against the tumour antigen ovalbumine prior to administration of mRNA coding for the TAP inhibitor delays tumour growth by 8 days compared to vaccination alone. Therefore the combination of vaccination and administration of the TAP inhibitor leads to a synergistic effect on tumour growth inhibition.

Figure 2:
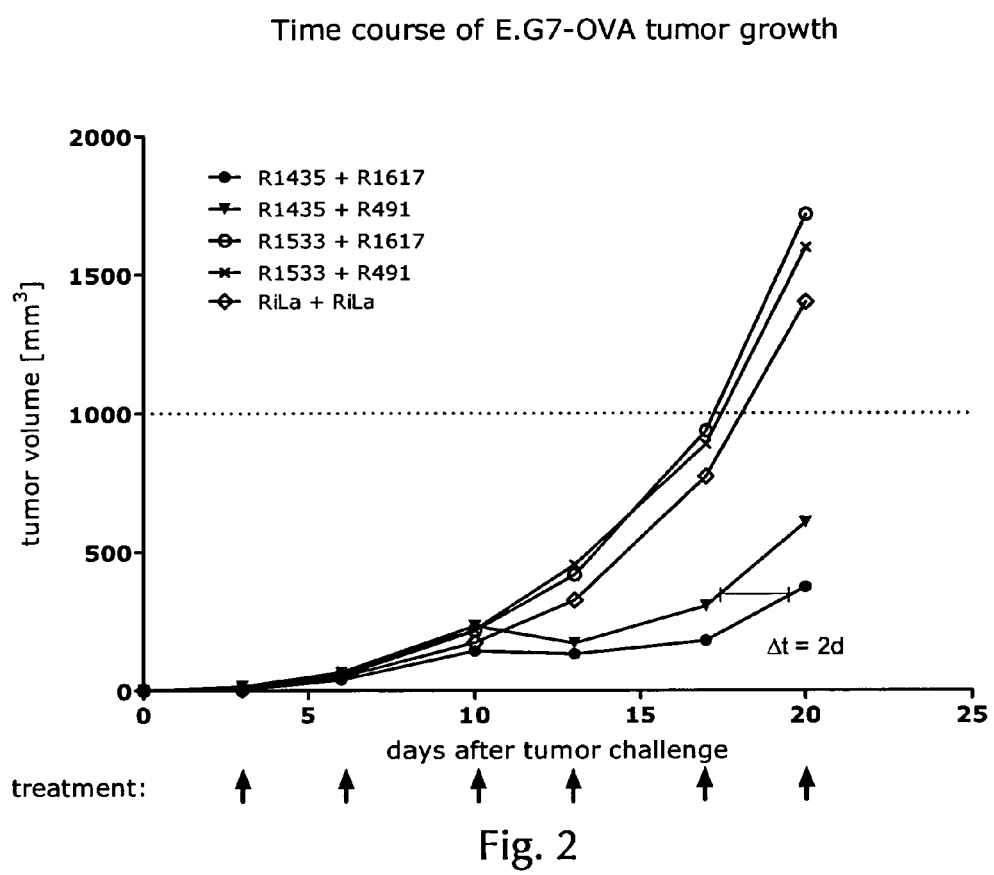

FIG. 2: shows the effect of the combination of vaccination against the tumour antigen ovalbumine and the administration of the TAP-Inhibitor UL49.5 on E.G7-OVA tumour growth. Here, vaccination against ovalbumin and administration of TAP inhibitor was conducted simultaneously at different administration sites in a therapeutic setting (after challenge with tumour cells). Expression of the TAP inhibitor alone has no effect on tumour growth, whereas simultaneous application of the vaccine/inhibitor combination delays tumor growth by 2 days compared to vaccination alone, indicating a synergistic effect on tumour growth inhibition.

FIG. 3: depicts the mRNA sequence of R1435 coding for *Gallus gallus* ovalbumine (SEQ ID NO: 1).

FIG. 4: depicts the mRNA sequence R1533/R491 coding for *Photinus pyralis* luciferase (SEQ ID NO: 2).

FIG. 5: depicts the mRNA sequence R1617 coding for the TAP-inhibitor UL49.5 (SEQ ID NO: 3).

EXAMPLES

The examples shown in the following are merely illustrative and shall describe the present invention in a further way. These examples shall not be construed to limit the present invention thereto.

1. Preparation of DNA and mRNA Constructs

For the present examples DNA sequences, encoding *Gallus gallus* ovalbumin mRNA (R1435) and TAP inhibitor UL49.5 mRNA (R1617) were prepared and used for subsequent in vitro transcription reactions. As control RNA mRNA coding for *Photinus pyralis* luciferase was used (R1533 and R491).

According to a first preparation, the DNA sequences coding for the above mentioned mRNAs were prepared. The constructs were prepared by modifying the wild type coding sequences by introducing a GC-optimized sequence for a better codon usage and stabilization, stabilizing sequences derived from alpha-globin-3'-UTR (muag (mutated alpha-globin-3'-UTR)), a stretch of 70× adenosine at the 3'-terminal end (poly-A-tail), a stretch of 30× cytosine at the 3'-terminal end (poly-C-tail). In SEQ ID NOs: 1-3 (see FIGS. 3-5) the sequences of the corresponding mRNAs are shown.

2. In Vitro Transcription:

The respective DNA plasmids prepared according to Example 1 were transcribed in vitro using T7 polymerase. Subsequently the mRNAs were purified using PureMessenger® (CureVac, Tilbingen, Germany).

3. Reagents:

Complexation Reagent:

protamine

4. Making of the Vaccine:

The mRNA used as adjuvant component of the vaccine in the experiments below was complexed with protamine by addition of protamine to the mRNA in the ratio (1:2) (w/w). After incubation for 10 min, the same amount of free mRNA used as antigen was added.

R1435 (vaccine): adjuvant component consisting of mRNA coding for *Gallus gallus* ovalbumine according to SEQ ID NO. 1 complexed with protamine in a ratio of 2:1 (w/w) and free mRNA coding for *Gallus gallus* ovalbumine (antigen mRNA) according to SEQ ID NO. 1 (ratio 1:1; complexed RNA:free RNA).

R1533 (control vaccine): adjuvant component consisting of mRNA coding for *Photinus pyralis* luciferase according to SEQ ID NO. 2 complexed with protamine in a ratio of 2:1 (w/w) and free mRNA coding for *Photinus pyralis* luciferase (antigen mRNA) according to SEQ ID NO 2 (ratio 1:1; complexed RNA:free RNA).

5. Immunization Experiments:

On the indicated days of the respective experiments C57BL/6 mice (8 mice per group) were vaccinated intradermally with the mRNA vaccines R1435 or R1533 (coding for *Gallus gallus* ovalbumine or *Photinus pyralis* luciferase as control, respectively). Injection was performed with 64 µg (experiment 1 (FIG. 1)) or 32 µg (experiment 2 (FIG. 2)) mRNA/mouse/day or Ringer-lactate as buffer control (RiLa).

6. Tumour Challenge:

On day o mice were challenged subcutaneously (right flank) with $1 \times 10^6$ (experiment 1 (FIG. 1)) or $0.3 \times 10^6$ (experiment 2 (FIG. 2)) E.G7-OVA cells per mouse (volume 100 µl in PBS).

Treatment with TAP Inhibitor:

On the indicated days of the respective experiments mice were intradermally injected with the mRNAs R1617 or R491 (coding for the TAP-inhibitor UL49.5 or *Photinus pyralis* luciferase as control respectively). For injections 50 g mRNA/mouse/day or Ringer-lactate as buffer control (RiLa) was used.

Monitoring of Tumour Growth:

Tumour growth was monitored by measuring the tumour size in 2 dimensions (length and width) using a calliper (starting on day 3 or 4). Tumour volume was calculated according to the following formula:

$$\text{volume}(\text{mm}^3) = \frac{\text{length}(\text{mm}) \times \pi \times \text{width}^2(\text{mm}^2)}{6}$$

The invention claimed is:

1. A method for stimulating an anti-tumor immune response in a subject having a cancer, comprising administering to a subject in need thereof an effective amount of:
   (a) a mRNA encoding an tumor cell antigen that is expressed in the cancer, wherein the antigen does not comprise an MHC class I heavy chain or β2m fusion protein; and
   (b) a mRNA encoding a TAP inhibitor.

2. The method of claim 1, wherein the mRNA encoding the antigen and the mRNA encoding the TAP inhibitor are administered at the same time.

3. The method of claim 1, wherein the mRNA encoding the TAP inhibitor and the mRNA encoding the antigen are administered at different times.

4. The method of claim 1, wherein the mRNA encoding the TAP inhibitor and the mRNA encoding the antigen are administered to the subject at different administration sites.

5. The method of claim 1, wherein the method does not further comprise administering an antigen presenting cell.

6. The method of claim 1, wherein the mRNA encoding the TAP inhibitor encodes the UL49.5 polypeptide.

7. The method of claim 1, wherein the mRNA encoding the antigen is administered before the mRNA encoding the TAP inhibitor.

8. The method of claim 1, wherein at least a portion of the mRNA encoding the antigen is complexed with protamine.

9. The method of claim 1, wherein the mRNA encoding the antigen or the mRNA encoding the TAP inhibitor is administered intradermally.

10. The method of claim 9, wherein the mRNA encoding the antigen and the mRNA encoding the TAP inhibitor are administered intradermally.

11. A method for stimulating an anti-tumor immune response in a subject having a cancer, comprising administering to a subject in need thereof an effective amount of:
    (a) a mRNA encoding a cancer or tumor cell antigen that is expressed in the cancer, wherein the antigen does not comprise an MHC class I heavy chain or β2m fusion protein; and
    (b) a mRNA encoding a TAP inhibitor comprising the UL49.5 polypeptide.

12. The method of claim 11, wherein the mRNA encoding a cancer or tumor cell antigen or the mRNA encoding a TAP inhibitor is administered intradermally.

13. The method of claim 12, wherein the mRNA encoding a cancer or tumor cell antigen and the mRNA encoding a TAP inhibitor are administered intradermally.

14. The method of claim 11, wherein the mRNA encoding the cancer or tumor cell antigen is administered before the mRNA encoding the TAP inhibitor.

15. The method of claim 11, wherein at least a portion of the mRNA encoding the cancer or tumor cell antigen is complexed with protamine.

16. The method of claim 11, wherein the mRNA encoding the TAP inhibitor and the mRNA encoding the cancer or tumor cell antigen are administered to the subject at different administration sites.

* * * * *

UNITED STATES PATENT AND TRADEMARK OFFICE
CERTIFICATE OF CORRECTION

PATENT NO.         : 9,737,595 B2
APPLICATION NO.    : 13/824502
DATED              : August 22, 2017
INVENTOR(S)        : Lorenz et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 902 days.

Signed and Sealed this
Twenty-fifth Day of September, 2018

Andrei Iancu
*Director of the United States Patent and Trademark Office*